(12) United States Patent
Edwards

(10) Patent No.: US 7,696,416 B2
(45) Date of Patent: Apr. 13, 2010

(54) NON-PUNGENT ORNAMENTAL PEPPERS

(76) Inventor: Marlin Edwards, 1912 Arena Dr., Davis, CA (US) 95618

( * ) Notice: Subject to any disclaimer, the term of this patent is extended or adjusted under 35 U.S.C. 154(b) by 27 days.

(21) Appl. No.: 12/139,296

(22) Filed: Jun. 13, 2008

(65) Prior Publication Data

US 2008/0250525 A1  Oct. 9, 2008

Related U.S. Application Data

(63) Continuation-in-part of application No. 11/247,632, filed on Oct. 11, 2005, now Pat. No. 7,393,995, and a continuation-in-part of application No. 09/564,153, filed on May 3, 2000, now Pat. No. 7,087,819.

(60) Provisional application No. 60/132,389, filed on May 4, 1999.

(51) Int. Cl.
*A01H 1/00* (2006.01)
*A01H 4/00* (2006.01)
*A01H 5/00* (2006.01)
*A01H 5/10* (2006.01)

(52) U.S. Cl. .................... 800/317.1; 435/410; 800/260; 800/265; 800/298

(58) Field of Classification Search ....................... None
See application file for complete search history.

(56) References Cited

U.S. PATENT DOCUMENTS 6,479,735 B1 * 11/2002 Araya et al. ................. 800/303

OTHER PUBLICATIONS

Heckenberger et al 2006, Molecular Breeding 17: 111-125.*
Berry et al 2002, Genetics 161: 819-824.*
Stokes Growers Guide 1991, p. 88.*

* cited by examiner

*Primary Examiner*—David H Kruse
(74) *Attorney, Agent, or Firm*—Jondle & Associates, P.C.

(57) ABSTRACT

The present invention relates to new, distinct and stable *Capsicum annuum* plants that have an ornamental phenotype and produce fruit that is non-pungent.

8 Claims, 8 Drawing Sheets

96P610 PEDIGREE

03P388-3 Pedigree

03P384-8 Pedigree

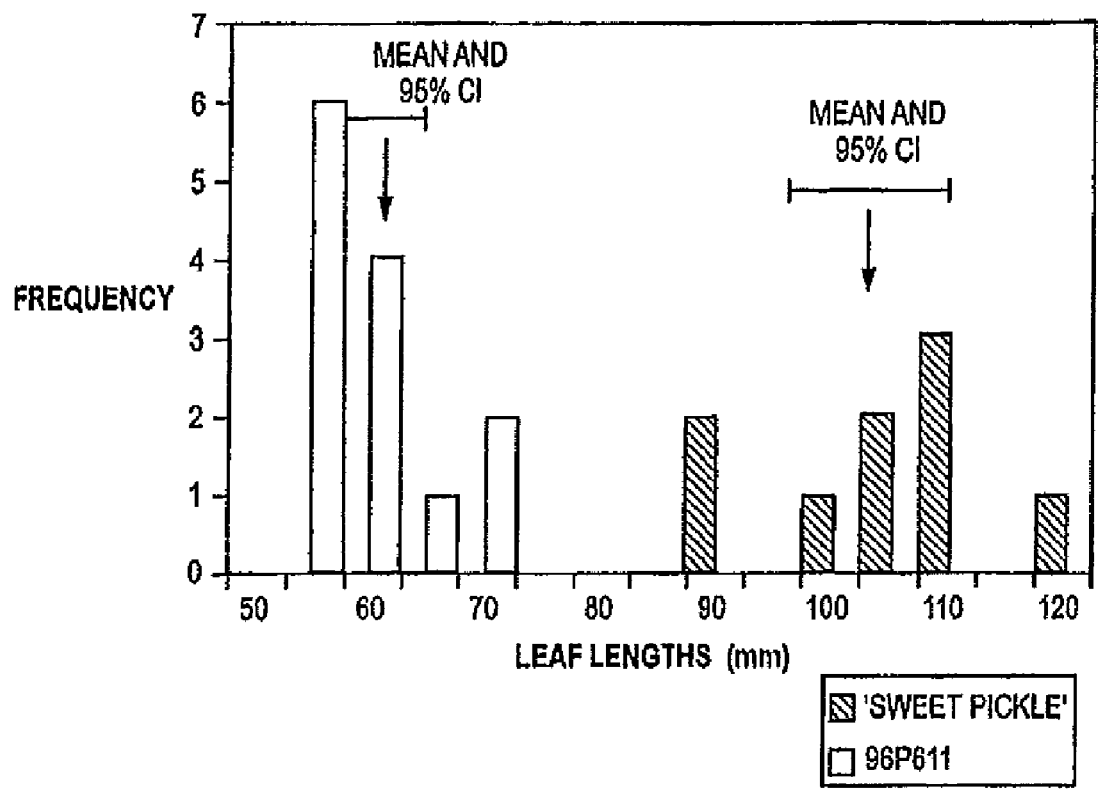

NON-PUNGENT ORNAMENTAL PEPPERS

This application is a continuation-in-part of U.S. application Ser. No. 11/247,632 filed on Oct. 11, 2005 which is a continuation-in-part of U.S. Pat. No. 7,087,819 issued on Aug. 8, 2006, which claims priority to U.S. Application No. 60/132,389 filed on May 4, 1999, all of which are incorporated herein by reference.

The present invention relates to a novel gene complex which confers an ornamental phenotype and results in fruit that is non-pungent in pepper cultivars of the genus *Capsicum*. This invention also relates to ornamental pepper seed, ornamental pepper plants, ornamental pepper varieties and ornamental pepper hybrids which contain this gene complex. In addition, the present invention also relates to methods for transferring this gene complex from sweet pepper varieties to ornamental pepper varieties and species and is useful for producing novel types and varieties of ornamental peppers which exhibit the ornamental phenotype and produce fruit that is phenotype.

Within the genus *Capsicum*, several cultivars possess an aesthetic value for ornamental purposes in the garden and as indoor pot plants. Ornamental peppers can provide a range of pod shapes and colors complemented by varying degrees of green or purple foliage. Classification of ornamental peppers includes cultivars within three species: *Capsicum annuum* L., *Capsicum* chinense Jacq., and *Capsicum pendulum* Willd. (See Corley, W. L. and A. H. Dempsey. 1972. *Ornamental Pepper Evaluation* 1965-1971. University of Georgia College of Agriculture Experiment Stations Research Report 136: 10 pp.).

Fruits of the ornamental peppers are edible but very pungent (See Corley, W. L. and A. H. Dempsey, Ornamental Pepper Evaluation 1965-1971. University of Georgia College of Agriculture Experiment Stations Research Report 136: 10 pp. (1972)). The pungent active ingredient found in peppers is the aromatic phenol capsaicin, which is capable of causing severe irritation. Capsaicin is produced by oil secreting glands located along the placenta. The presence or absence of pungency in *Capsicum* is reported to have simple trait inheritance with pungency partially dominant to non-pungency (See Deshpande, R. B., *Indian Journal of Agricultural Science,* 5:5 13-516 (1945). The degree of pungency within a genotype is subject to unidentified genetic factors and the environment, in particular temperature (See, Lipper, L. F., et al., The Botanical Review, 32:24-55 (1966)).

Non-pungency is a characteristic of the Grossum Group of *Capsicum annuum* L. var. *annuum*, containing the commonly known peppers Bell Pepper, Sweet Pepper or Green Pepper (*Hortus Third A Concise Dictionary of Plants Cultivated in the United States and Canada*, MacMillan Publishing Company 1976). It would be desirable to have non-pungent ornamental peppers thereby eliminating possible hazards from capsaicin in the landscape or indoor environment.

SUMMARY OF THE PRESENT INVENTION

The present invention relates to non-pungent ornamental *Capsicum annuum* plants or varieties which produce fruit (i.e., peppers), that contain capsaicin levels which are statistically equal to or less than the capsaicin levels of fruit (i.e., peppers) obtained from commercial sweet green *Capsicum annuum* plants at the $\alpha=0.05$ confidence level.

More specifically, in one embodiment, the present invention relates to *Capsicum annuum* plants that produce fruit that is non-pungent, meaning that said fruit has a capsaicin level no greater than 500 Scoville Heat Units. In addition, said plants have a height of less than about 29.0 cm. Moreover, in another embodiment, the present invention further relates to parts of these *Capsicum annuum* plants, such as, but not limited to, seed, flowers, pollen, ovules, buds, shoots, cuttings, petals, leaves, stems, roots, tissues or combinations thereof.

The ornamental *Capsicum annuum* plants of the present invention contain a gene complex which confers the trait of non-pungency to the fruit produced by said plants. In addition, the ornamental *Capsicum annuum* plants exhibit an overall ornamental phenotype when compared to commercial sweet green *Capsicum annuum* plants.

Examples of ornamental *Capsicum annuum* plants containing such a gene complex, which when expressed, confers non-pungency to the fruit and which have an overall ornamental phenotype, are the *Capsicum annuum* plants known as 96P601, 96P631, 96P610, 97P1938, 03P388-3, 03P384-8 and PA47. The present invention also relates to parts such as, but not limited to, seed, flowers, pollen, ovules, buds, shoots, cuttings, petals, leaves, stems, roots, tissues or combinations thereof, produced by the non-pungent ornamental *Capsicum annuum* plants of the present invention. Moreover, the present invention also relates to a tissue culture comprising regenerable cells of the non-pungent ornamental *Capsicum annuum* plants of the present invention.

Additionally, in another embodiment, the present invention relates to ornamental *Capsicum annuum* seed containing a gene complex which when planted and regenerated into plants, produces a plant having an ornamental phenotype and which produces fruit that is non-pungent. Specifically, examples of ornamental pepper seed containing such a gene complex is seed obtained from *Capsicum annuum* plants known as 96P601, 96P631, 96P610, 97P1938, 03P388-3, 03P384-8 and PA47. The present invention also relates to ornamental *Capsicum annuum* plants produced by planting and growing seed of the present invention. These ornamental *Capsicum annuum* plants have an ornamental phenotype and produce fruit that contain capsaicin levels which are statistically equal to or less than the capsaicin levels of peppers obtained from commercial sweet green pepper *Capsicum annuum* plants at the $\alpha=0.05$ confidence level. More specifically, said fruit has a capsaicin level not greater than 500 Scoville Heat Units.

Also, in another embodiment, the present invention relates to non-pungent ornamental *Capsicum annuum* peppers (i.e., fruit) that have capsaicin levels which are statistically equal to or less than the capsaicin levels of peppers derived from commercial sweet green *Capsicum annuum* pepper cultivars at the $\alpha=0.05$ confidence level. More specifically, the non-pungent peppers of the present invention have a capsaicin level of not greater than 500 Scoville Heat Units.

In yet another embodiment, the present invention relates to a method for transferring one or more genes that confer non-pungency to fruit of a *Capsicum annuum* from sweet *Capsicum annuum* plants to ornamental *Capsicum annuum* plants. Methods for transferring such a gene or genes are well known in the art. For example, the method can involve the steps of crossing a non-pungent sweet non-ornamental or ornamental *Capsicum annuum* plant containing a gene for non-pungency with a pungent ornamental *Capsicum annuum* plant. Seeds resulting from this cross are then collected and regenerated into plants. *Capsicum annuum* plants containing a gene complex, namely those exhibiting an ornamental phenotype and that produce fruit that is non-pungent, are selected from the regenerated plants. The method also involves crossing the selected non-pungent ornamental *Capsicum annuum* plant containing this gene complex which confers non-pungency and ornamental attributes with other non-pungent ornamental peppers containing a gene complex which confers non-pungency and ornamental attributes or with pungent ornamental pepper plants having commercially desirable phenotypic traits for a sufficient number of generations to obtain a non-pungent ornamental pepper plant containing the gene complex which confers non-pungency and a desirable ornamental phenotype.

Additionally, in yet another embodiment, the present invention involves a method of producing *Capsicum annuum* seed. The method involves a number of steps. One step involves crossing a first *Capsicum annuum* plant with a second *Capsicum annuum* plant and harvesting the resultant *Capsicum annuum* seed. Either the first or second *Capsicum annuum* plant is a *Capsicum annuum* plant having a height of less than about 29.0 cm and which produces fruit having a capsaicin level not greater than 500 Scoville Units or a part thereof or a descendant of a *Capsicum annuum* plant having a height of less than about 29.0 cm and which produces fruit having a capsaicin level not greater than 500 Scoville Units. The method further comprises the step of planting the resultant *Capsicum annuum* seed and selecting a *Capsicum annuum* plant having a height equal to or less than about 29.0 cm or upright fruit wherein the capsaicin levels of said fruit is not greater than about 500 Scoville Heat Units. The method can further comprise the step of collecting the seed of the selected plant. The present invention also relates to a *Capsicum annuum* plant having a height of less than about 29.0 cm and which produces fruit having a capsaicin level not greater than 500 Scoville Units that is produced by the method described herein.

In still a further embodiment, the present invention also relates to a method of producing a *Capsicum annuum* plant in a pepper breeding program. The method can involve the following steps. The first step involves obtaining a *Capsicum annuum* plant having a height of less than about 29.0 cm and which produces fruit having a capsaicin level not greater than 500 Scoville Units or a part thereof or a descendant of a *Capsicum annuum* plant having a height of less than about 29.0 cm and which produces fruit having a capsaicin level not greater than 500 Scoville Units or a part thereof as a source of breeding material. The next step involves employing the above described *Capsicum annuum* plant as a source of plant breeding material in a plant breeding program using plant breeding techniques (including, but not limited to pedigree breeding, recurrent selection, backcrossing, or combinations of crossing, self-pollination and/or backcrossing) to produce a *Capsicum annuum* plant. Preferably, the *Capsicum annuum* plant produced and selected as a result of this method has a height of less than about 29.0 cm and produces fruit having a capsaicin level not greater than 500 Scoville Units. The method can further comprise the step of collecting seed of the *Capsicum annuum* plant produced as a result of said method. The present invention also relates to a *Capsicum annuum* plant having a height of less than about 29.0 cm and which produces fruit having a capsaicin level not greater than 500 Scoville Units that is produced by the method described herein.

In yet another embodiment, the present invention relates to viable non-pungent ornamental *Capsicum annuum* seeds (1) designated 96P610, a representative sample of which have been deposited under ATCC Accession Number 203779; (2) designated 97P1938, a representative sample of which has been deposited under ATCC Accession Number PTA-5749; (3) designated P96P611, a representative sample of which has been deposited under ATCC Accession Number PTA-5689; and (4) designated PA47, a representative sample of which has been deposited under ATCC Accession Number PTA-8808. The present invention further relates to plants grown from representative seeds designated 96P610, 97P1938, P96P611 or PA47 and to methods of using these plants in breeding to produce *Capsicum annuum* plants having an ornamental phenotype and which produce fruit that is non-pungent and *Capsicum annuum* plants having an ornamental phenotype and fruit that is non-pungent that are derived or have a pedigree that includes plants grown from seeds designated 96P610, 97P1938, P96P611 or PA47.

In still another embodiment, the present invention relates to a method of producing *Capsicum annuum* seed. The method comprises the following steps: crossing a first *Capsicum annuum* plant with a second *Capsicum annuum* plant and harvesting the resultant *Capsicum annuum* seed, wherein said first or second *Capsicum annuum* plant is a *Capsicum annuum* plant or a part thereof grown from seed designated as 96P610, a representative sample of which is deposited under ATCC Accession Number 203779 or a descendant of the *Capsicum annuum* plant or a part thereof grown from seed designated as 96P610, a representative sample of which is deposited under ATCC Accession Number 203779.

This method can further comprise the step of planting the resultant *Capsicum annuum* seed and selecting a *Capsicum annuum* plant having a height equal to or less than about 29.0 cm or upright fruit wherein the capsaicin levels of said fruit is not greater than about 500 Scoville Heat Units. Additionally, the method can still further comprise the step of collecting the seed of the selected plant.

Additionally, the present invention also relates to a *Capsicum annuum* plant having a height of less than about 29.0 cm and which produces fruit having a capsaicin level not greater than 500 Scoville Units produced by this hereinbefore described method.

In another embodiment, the present invention relates to a method of producing a *Capsicum annuum* plant in a pepper breeding program. The method comprises the following steps:

a) obtaining a *Capsicum annuum* plant or a part thereof grown from seed designated as 96P610, a representative sample of which is deposited under ATCC Accession Number 203779 or a descendant of the *Capsicum annuum* plant or a part thereof grown from seed designated as 96P610, a representative sample of which is deposited under ATCC Accession Number 203779, as a source of breeding material; and b) employing the *Capsicum annuum* plant obtained in step a) as a source of plant breeding material in a plant breeding program using plant breeding techniques to produce a *Capsicum annuum* plant.

In the above method, the plant breeding techniques can be recurrent selection, backcrossing, pedigree breeding, combinations of these techniques or combinations of portions of these techniques. Additionally, the hereinbefore described method can further comprise the step of selecting a *Capsicum annuum* plant having a height equal to or less than about 29.0 cm or upright fruit wherein the capsaicin levels of said fruit is not greater than about 500 Scoville Heat Units. Additionally, the method can further comprise selecting the seed of the selected plant.

Additionally, the present invention also relates to a *Capsicum annuum* plant having a height of less than about 29.0 cm and which produces fruit having a capsaicin level not greater than 500 Scoville Units produced by this hereinbefore described method.

In another embodiment, the present invention relates to a method of producing *Capsicum annuum* seed. The method comprises the following steps: crossing a first *Capsicum*

*annuum* plant with a second *Capsicum annuum* plant and harvesting the resultant *Capsicum annuum* seed, wherein said first or second *Capsicum annuum* plant is a *Capsicum annuum* plant or a part thereof grown from seed designated as 96P611, a representative sample of which is deposited under ATCC Accession Number PTA-5689 or a descendant of the *Capsicum annuum* plant or a part thereof grown from seed designated as 96P611, a representative sample of which is deposited under ATCC Accession Number PTA-5689.

This method can further comprise the step of planting the resultant *Capsicum annuum* seed and selecting a *Capsicum annuum* plant having a height equal to or less than about 29.0 cm or upright fruit wherein the capsaicin levels of said fruit is not greater than about 500 Scoville Heat Units. Additionally, the method can still further comprise the step of collecting the seed of the selected plant.

Additionally, the present invention also relates to a *Capsicum annuum* plant having a height of less than about 29.0 cm and which produces fruit having a capsaicin level not greater than 500 Scoville Units produced by this hereinbefore described method.

In another embodiment, the present invention relates to a method of producing a *Capsicum annuum* plant in a pepper breeding program. The method comprises the following steps:

a) obtaining a *Capsicum annuum* plant or a part thereof grown from seed designated as 96P611, a representative sample of which is deposited under ATCC Accession Number PTA-5689 or a descendant of the *Capsicum annuum* plant or a part thereof grown from seed designated as 96P611, a representative sample of which is deposited under ATCC Accession Number PTA-5689, as a source of breeding material; and b) employing the *Capsicum annuum* plant obtained in step a) as a source of plant breeding material in a plant breeding program using plant breeding techniques to produce a *Capsicum annuum* plant.

In the above method, the plant breeding techniques can be recurrent selection, backcrossing, pedigree breeding, combinations of these techniques or combinations of portions of these techniques. Additionally, the hereinbefore described method can further comprise the step of selecting a *Capsicum annuum* plant having a height equal to or less than about 29.0 cm or upright fruit wherein the capsaicin levels of said fruit is not greater than about 500 Scoville Heat Units. Additionally, the method can further comprise selecting the seed of the selected plant.

Additionally, the present invention also relates to a *Capsicum annuum* plant having a height of less than about 29.0 cm and which produces fruit having a capsaicin level not greater than 500 Scoville Units produced by this hereinbefore described method.

In another embodiment, the present invention relates to a method of producing *Capsicum annuum* seed. The method comprises the following steps: crossing a first *Capsicum annuum* plant with a second *Capsicum annuum* plant and harvesting the resultant *Capsicum annuum* seed, wherein said first or second *Capsicum annuum* plant is a *Capsicum annuum* plant or a part thereof grown from seed designated as 97P1938, a representative sample of which is deposited under ATCC Accession Number PTA-5749 or a descendant of the *Capsicum annuum* plant or a part thereof grown from seed designated as 97P1938, a representative sample of which is deposited under ATCC Accession Number PTA-5749.

This method can further comprise the step of planting the resultant *Capsicum annuum* seed and selecting a *Capsicum annuum* plant having a height equal to or less than about 29.0 cm or upright fruit wherein the capsaicin levels of said fruit is not greater than about 500 Scoville Heat Units. Additionally, the method can still further comprise the step of collecting the seed of the selected plant.

Additionally, the present invention also relates to a *Capsicum annuum* plant having a height of less than about 29.0 cm and which produces fruit having a capsaicin level not greater than 500 Scoville Units produced by this hereinbefore described method.

In another embodiment, the present invention relates to a method of producing a *Capsicum annuum* plant in a pepper breeding program. The method comprises the following steps:

a) obtaining a *Capsicum annuum* plant or a part thereof grown from seed designated as 97P1938, a representative sample of which is deposited under ATCC Accession Number PTA-5749 or a descendant of the *Capsicum annuum* plant or a part thereof grown from seed designated as 97P1938, a representative sample of which is deposited under ATCC Accession Number PTA-5749, as a source of breeding material; and b) employing the *Capsicum annuum* plant obtained in step a) as a source of plant breeding material in a plant breeding program using plant breeding techniques to produce a *Capsicum annuum* plant.

In the above method, the plant breeding techniques can be recurrent selection, backcrossing, pedigree breeding, combinations of these techniques or combinations of portions of these techniques. Additionally, the hereinbefore described method can further comprise the step of selecting a *Capsicum annuum* plant having a height equal to or less than about 29.0 cm or upright fruit wherein the capsaicin levels of said fruit is not greater than about 500 Scoville Heat Units. Additionally, the method can further comprise selecting the seed of the selected plant.

Additionally, the present invention also relates to a *Capsicum annuum* plant having a height of less than about 29.0 cm and which produces fruit having a capsaicin level not greater than 500 Scoville Units produced by this hereinbefore described method.

In another embodiment, the present invention relates to a method of producing *Capsicum annuum* seed. The method comprises the following steps: crossing a first *Capsicum annuum* plant with a second *Capsicum annuum* plant and harvesting the resultant *Capsicum annuum* seed, wherein said first or second *Capsicum annuum* plant is a *Capsicum annuum* plant or a part thereof grown from seed designated as PA47, a representative sample of which is deposited under ATCC Accession Number PTA-8808 or a descendant of the *Capsicum annuum* plant or a part thereof grown from seed designated as PA47, a representative sample of which is deposited under ATCC Accession Number PTA-8808.

This method can further comprise the step of planting the resultant *Capsicum annuum* seed and selecting a *Capsicum annuum* plant having a height equal to or less than about 29.0 cm or upright fruit wherein the capsaicin levels of said fruit is not greater than about 500 Scoville Heat Units. Additionally, the method can still further comprise the step of collecting the seed of the selected plant.

Additionally, the present invention also relates to a *Capsicum annuum* plant having a height of less than about 29.0 cm and which produces fruit having a capsaicin level not greater than 500 Scoville Units produced by this hereinbefore described method.

In yet still another embodiment, the present invention relates to a method of producing a *Capsicum annuum* plant in a pepper breeding program. The method comprises the following steps:

a) obtaining a *Capsicum annuum* plant or a part thereof grown from seed designated as PA47, a representative sample of which is deposited under ATCC Accession Number PTA-8808 or a descendant of the *Capsicum annuum* plant or a part thereof grown from seed designated as PA47, a representative sample of which is deposited under ATCC Accession Number PTA-8808, as a source of breeding material; and b) employing the *Capsicum annuum* plant obtained in step a) as a source of plant breeding material in a plant breeding program using plant breeding techniques to produce a *Capsicum annuum* plant.

In the above method, the plant breeding techniques can be recurrent selection, backcrossing, pedigree breeding, combinations of these techniques or combinations of portions of these techniques. Additionally, the hereinbefore described method can further comprise the step of selecting a *Capsicum annuum* plant having a height equal to or less than about 29.0 cm or upright fruit wherein the capsaicin levels of said fruit is not greater than about 500 Scoville Heat Units. Additionally, the method can further comprise selecting the seed of the selected plant.

Additionally, the present invention also relates to a *Capsicum annuum* plant having a height of less than about 29.0 cm and which produces fruit having a capsaicin level not greater than 500 Scoville Units produced by this hereinbefore described method.

According to the invention, there is provided a new *Capsicum annuum* hybrid designated PA47. This invention thus relates to the seeds of *Capsicum annuum* hybrid PA47, to the plants of *Capsicum annuum* hybrid PA47 and to methods for producing a *Capsicum annuum* plant produced by crossing hybrid PA47 with itself or another *Capsicum annuum* variety, and the creation of variants by mutagenesis or transformation of *Capsicum annuum* hybrid PA47.

Parts of the pepper plant PA47 are also provided, such as e.g., fruits, leaves, stems, flowers, pollen and ovules.

Another aspect of the invention is to provide methods for producing other pepper plants derived from pepper cultivar PA47. Pepper cultivars derived by the use of those methods are also part of the invention.

In another aspect, the present invention provides for single or multiple gene converted plants of *Capsicum annuum* hybrid PA47. The transferred gene(s) may preferably be a dominant or recessive allele. Preferably, the transferred gene(s) will confer such traits as herbicide resistance, insect resistance, resistance for bacterial, fungal, or viral disease, male fertility, male sterility, pest resistance and desirable ornamental characteristics such as plant height, fruit size, fruit weight, fruit color, and capsaicin level. The gene may be a naturally occurring *Capsicum annuum* gene or a transgene introduced through genetic engineering techniques.

In another aspect, the present invention provides regenerable cells for use in tissue culture of any one of *Capsicum annuum* variety 96P610, 97P1938, 96P611 or PA47. The tissue culture will preferably be capable of regenerating plants having all the physiological and morphological characteristics of the foregoing any one of *Capsicum annuum* variety 96P610, 97P1938, 96P611 or PA47 plants, and of regenerating plants having substantially the same genotype as the foregoing any one of *Capsicum annuum* variety 96P610, 97P1938, 96P611 or PA47 plants. Preferably, the regenerable cells in such tissue cultures will be embryos, protoplasts, meristematic cells, callus, pollen, leaves, anthers, cotyledons, hypocotyl, pistils, roots, root tips, flowers, seeds, petiole, fruits or stems. Still further, the present invention provides *Capsicum annuum* plants regenerated from the tissue cultures of the invention.

The invention further provides methods for developing pepper plants including both inbreds and hybrids derived from pepper hybrid PA47, in a pepper plant breeding program using plant breeding techniques including recurrent selection, backcrossing, pedigree breeding, restriction fragment length polymorphism enhanced selection, genetic marker enhanced selection and transformation. Marker loci such as restriction fragment polymorphisms or random amplified DNA have been published for many years and may be used for selection (See Pierce et al., *HortScience* (1990) 25:605-615, Wehner, T., *Cucurbit Genetics Cooperative Report*, (1997) 20: 66-88 and Kennard et al., *Theoretical Applied Genetics* (1994) 89:217-224). Seeds, pepper plants, and parts thereof produced by such breeding methods are also part of the invention.

BRIEF DESCRIPTION OF THE FIGURES

FIG. 9 shows a comparison of the leaf lengths of 'Sweet Pickle' and cultivar 96P611 of the present invention.

DETAILED DESCRIPTION OF THE INVENTION

Figure 1:
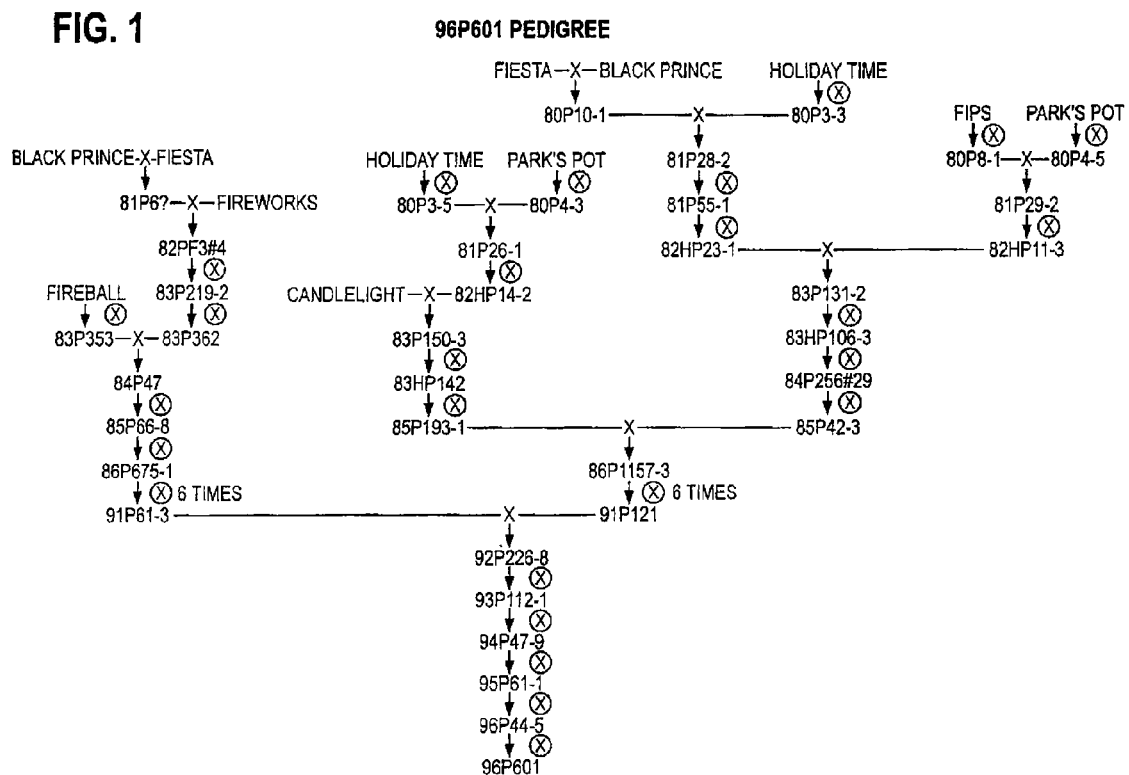
FIG. 1 shows the pedigree of *Capsicum annuum* cultivar 96P601 which has an ornamental phenotype and produces fruit that is non-pungent.

The present invention relates to ornamental *Capsicum annuum* plants that produce fruit (peppers) that are non-pungent. More specifically, the inventor of the present invention has discovered a transferable gene complex, which when introgressed into *Capsicum annuum* germplasm, results in the *Capsicum annuum* plants of the present invention that exhibit an ornamental phenotype and that produce fruit (peppers) that are non-pungent. This gene complex can be incorporated into many other genetic backgrounds.

The terms "non-pungency" or "non-pungent" as used herein in connection with the *Capsicum annuum* fruit of the present invention refer to the level of capsaicin present in *Capsicum annuum* fruit as measured in Scoville Heat Units. Methods for determining the level of capsaicin in *Capsicum annuum* fruit is well known to those in the art and includes, but is not limited to, the use of high performance liquid chromatography (HPLC). *Capsicum annuum* fruit is considered to be "non-pungent" if the capsaicin levels in said fruit are statistically equal to or less than the capsaicin levels of fruit derived from a commercial sweet green *Capsicum* cultivar at the $a=0.05$ confidence level. Sweet green *Capsicum annuum* fruit, while not produced for the ornamental market, can be used as a non-pungent benchmark based on their classification in the non-pungent *Capsicum grossum* Group (See *Hortus Third A Concise Dictionary of Plants Cultivated in the United States and Canada*, MacMillan Publishing Company 1976, herein incorporated by reference). More specifically, the *Capsicum annuum* fruit of the present invention contain a level of capsaicin that is not greater than 500 Scoville Heat Units.

As used herein, the terms "ornamental pepper plant", "ornamental *Capsicum annuum* plant" or "ornamental phenotype" refer to a *Capsicum annuum* plant possessing at least one ornamental characteristic, such as fruit number, fruit weight, plant height, branching, leaf length and leaf width, and capsaicin level that is not statistically less desirable than those of commercially available pungent ornamental *Capsicum annuum* plants. Examples of pungent ornamental *Capsicum annuum* plants include, but are not limited to, 'Red Missile', 'Holiday Flame' and 'Masquerade' all available from Ball Horticultural Company, 622 Town Road, West Chicago, Ill., 60185. Preferably, the *Capsicum annuum* plants of the present invention have an ornamental phenotype that is illustrated by plants that exhibit a total plant height equal to or less than about 29.0 cm or upright, non-pungent fruit or a combination of upright, non-pungent fruit and a total plant height equal to or less than about 29.0 cm. For example, plants known as 96P610, 97P1938, P96P611, 03P388-3, 03P384-8, and PA47 which are described in more detail herein, each possess an ornamental phenotype and have a plant height equal to or less than about 29.0 cm, and upright, non-pungent fruit.

As used herein, the term "gene complex" refers to a gene(s) or allele(s) which when introgressed or transferred into a *Capsicum annuum* plant that does not contain said gene(s) or allele(s) results in a *Capsicum annuum* plant produces a *Capsicum annuum* plant that has an ornamental phenotype and that produces fruit that is non-pungent. The gene complex described herein may be transferred into a *Capsicum annuum* plant which does not contain the gene complex using any techniques known in the art, such as by traditional breeding techniques (including, but not limited to, pedigree breeding, recurrent selection, backcrossing, etc.), mutagenesis, genetic transformation or engineering, combinations of crossing, self-pollination and/or backcrossing. Specifically, one or more genes comprising the gene complex can be inserted in the antisense direction in an expression construct using techniques well-known in the art, in order to "knock-out" capsaicin production.

The ornamental *Capsicum annuum* cultivars of the present invention are genetically stable. Additionally, the gene complex described herein can be bred into diverse ornamental *Capsicum* backgrounds, using any techniques known in the art, such as by traditional breeding techniques (including, but not limited to, pedigree breeding, recurrent selection, backcrossing, etc.), mutagenesis, genetic transformation or engineering, combinations of crossing, self-pollination and/or backcrossing.

As previously discussed, the *Capsicum annuum* plants of the present invention, which exhibit an ornamental phenotype and produce fruit that is non-pungent, are genetically stable, as evidenced by the stability of these traits through sexual crosses. Nonetheless, depending upon the cultivar, the level of capsaicin and thus the degree of pungency per fruit in a single plant or in multiple plants may be adversely affected by environmental stress factors and may vary, without any variance in the genotype of the plant. Environmental stress factors which may adversely affect the level of capsaicin and thus degree of pungency per fruit include, but are not limited to, high temperatures, low soil fertility or water stress.

The non-pungent ornamental *Capsicum annuum* cultivars of the present invention maintain functional male and female organs, thus making the incorporation of the ornamental phenotype and the trait of non-pungency of the fruit into other ornamental pepper cultivars possible. The trait of non-pungency of the fruit may be incorporated into cultivars having a range of pod shapes and colors complemented by varying degrees of green or purple foliage.

It is expected that the trait of non-pungency of the fruit can be predictably transferred into any ornamental *Capsicum* background using the techniques known in the art and described herein. For example, traditional breeding techniques such as pedigree breeding, backcrossing and recurrent selection for progeny having fruit that is non-pungent and an ornamental phenotype can be bred into diverse ornamental *Capsicum annuum* backgrounds. Intermating of superior genotypes which exhibit ornamental phenotypes and produce non-pungent fruit through repeated generations has resulted in the selection of cultivars with improved ornamental phenotypes that produce non-pungent fruit. Periodic outcrossing can be done during the breeding program in order to introduce desirable characteristics and to circumvent inbreeding depression.

It is expected that any selected *Capsicum annuum* pepper cultivar having an ornamental phenotype and that produces non-pungent fruit can be produced as progeny from sexual crosses and sold as seed. Methods for the storage of such seed are well known in the art.

The present invention also relates to a method of transferring a gene for non-pungency of the fruit from a sweet pepper plant to a pungent ornamental pepper plant. The method involves the steps of crossing a sweet pepper plant containing a gene for non-pungency of the fruit with a pungent ornamental pepper plant. The seeds resulting from the cross are collected, planted and regenerated into plants. Non-pungent ornamental pepper plants which contain the gene complex which confers non-pungency to the fruit and an ornamental phenotype are then selected from the regenerated plants. In addition, the method further involves crossing the selected non-pungent ornamental pepper plants containing the gene complex which confers non-pungency to the fruit and an ornamental phenotype with other non-pungent ornamental pepper plants containing the gene complex which confers non-pungency to the fruit and an ornamental phenotype or with pungent ornamental pepper plants having commercially desirable phenotypic traits for a sufficient number of generations, to obtain non-pungent ornamental pepper plants containing the gene complex which confers non-pungency to the fruit and a desirable ornamental phenotype.

This previously unknown non-pungent ornamental pepper characteristic arose from breeding and research efforts. The gene that encodes for non-pungent fruit originated from two sweet green pepper sources, which are identified as 'Park's Pot' and 'California Wonder'. 'Park's Pot' is a bell pepper cultivar that was intended for pot plant culture and has large, bell-shaped fruit and is commercially available from Geo. W. Park Seed Co. Inc., 1 Parkton Avenue, Greenwood, S.C., 29647. 'California Wonder' has large, green, pendent, sweet, three to four lobed, bell-shaped peppers and is commercially available from The Pepper Gal, P.O. Box 23006, Fort Lauderdale, Fla. 33311.

By way of example, and not of limitation, examples of the present invention will now be given.

Example 1

Pedigree for Non-Pungent Ornamental Pepper Cultivar 96P601

FIG. 1 shows the pedigree that lead to non-pungent ornamental *Capsicum annuum* cultivar 96P601. Plants of 96P601 have a height that is less than or equal to 29.0 cm and fruit that is non-pungent. More specifically, the fruit produced by plants of *Capsicum annuum* plant 96P601 have a capsaicin level not greater than 500 Scoville Heat Units. Plants of 96P601 or parts from this plant, such as parts of these *Capsicum* annum plants, such as, but not limited to, seed, flowers, pollen, ovules, buds, shoots, cuttings, petals, leaves, stems, roots, tissues or combinations thereof, can be used to produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, 96P601 can be crossed, as either a male or female parent plant with a second *Capsicum annuum* plant. After said crossing, the resulting *Capsicum annuum* seed is harvested and grown into *Capsicum annuum* plants. *Capsicum annuum* plants which have a height equal to or less than about 29.0 cm and that have fruit having capsaicin levels not greater than about 500 Scoville Heat Units are then selected. Methods for determining the levels of capsaicin in fruit, such as a pepper, are well known to those skilled in the art.

Plants that have a height equal to or less than about 29.0 cm and that have fruit having capsaicin levels not greater than about 500 Scoville Heat Units, that are produced by the above method and that are selected, are considered to be descendants of 96P601 (hereinafter referred to as "Descendant(s)"). Such Descendants can used to produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, a Descendant or a part from a Descendant, such as parts of these *Capsicum annuum* plants, such as, but not limited to, seed, flowers, pollen, ovules, buds, shoots, cuttings, petals, leaves, stems, roots, tissues or combinations thereof, can be crossed, as either a male or female parent plant with a second *Capsicum annuum* plant. After said crossing, the resulting *Capsicum annuum* seed is harvested and grown into *Capsicum annuum* plants. *Capsicum annuum* plants which have a height equal to or less than about 29.0 cm and that have fruit having capsaicin levels not greater than about 500 Scoville Heat Units are then selected. Methods for determining the levels of capsaicin in fruit, such as a pepper, are well known to those skilled in the art. As those skilled in the art can appreciate, such breeding and selection methods described above can be repeated over and over to produce a variety of new, stable *Capsicum annuum* plants having a height equal to or less than about 29.0 cm and that have fruit having capsaicin levels not greater than about 500 Scoville Heat Units.

Example 2

Pedigree for Non-Pungent Ornamental Pepper Cultivar 96P631

Figure 2:
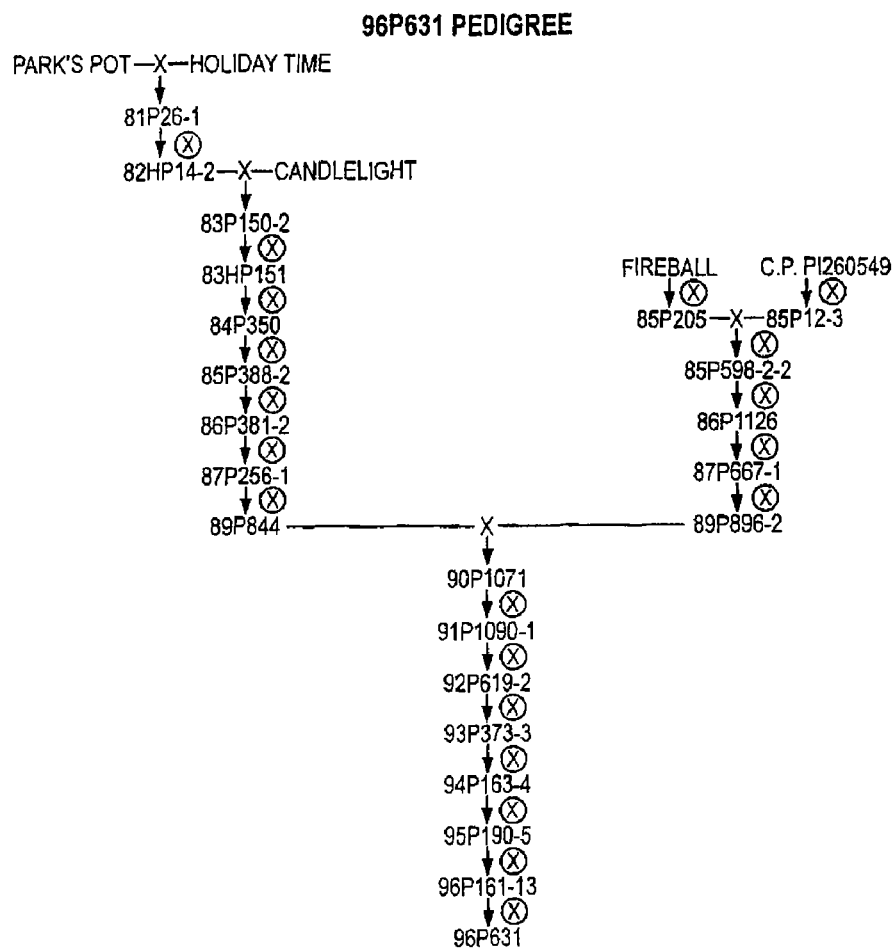
FIG. 2 shows the pedigree of *Capsicum annuum* cultivar 96P631 which has an ornamental phenotype and produces fruit that is non-pungent.

FIG. 2 shows the pedigree that lead to non-pungent ornamental *Capsicum annuum* cultivar 96P631. Plants of 96P631 have a height that is less than or equal to 29.0 cm and fruit that is non-pungent. More specifically, the fruit produced by plants of *Capsicum annuum* plant 96P631 have a capsaicin level not greater than 500 Scoville Heat Units. Plants of 96P631 or parts from this plant, such as parts of these *Capsicum* annum plants, such as, but not limited to, seed, flowers, pollen, ovules, buds, shoots, cuttings, petals, leaves, stems, roots, tissues or combinations thereof, can be used in produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, pollen obtained from 96P631 can be placed on the stigma of a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. Methods for determining the levels of capsaicin in fruit, such as a pepper, are well known to those skilled in the art.

Plants that have a height equal to or less than about 29.0 cm and that have fruit having capsaicin levels not greater than about 500 Scoville Heat Units, that are produced by the above method and that are selected, are considered to be descendants of 96P631 (hereinafter referred to as "Descendant(s)"). Such Descendants can used to produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, a Descendant or a part from a Descendant, such as parts of these *Capsicum annuum* plants, such as, but not limited to, seed, flowers, pollen, ovules, buds, shoots, cuttings, petals, leaves, stems, roots, tissues or combinations thereof, can be crossed, as either a male or female parent plant with a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. Methods for determining the levels of capsaicin in fruit, such as a pepper, are well known to those skilled in the art. As those skilled in the art can appreciate, such breeding and selection methods described above can be repeated over and over to produce a variety of new *Capsicum annuum* plants having a height equal to or less than about 29.0 cm and that have fruit having capsaicin levels not greater than about 500 Scoville Heat Units.

Example 3

Pedigree for Non-Pungent Ornamental Pepper Cultivar 96P610

Figure 3:
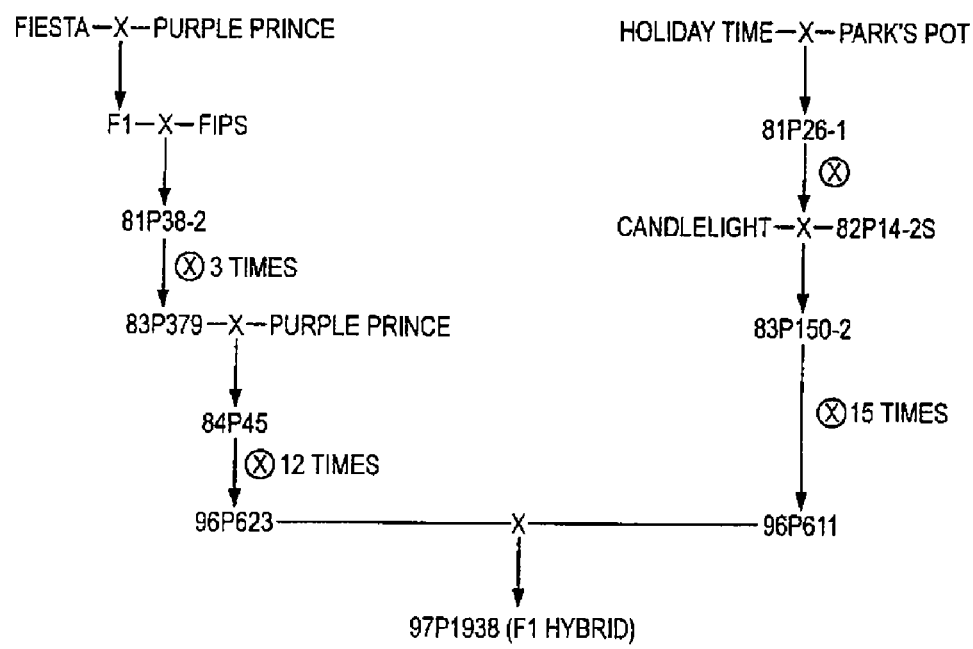
FIG. 3 shows the pedigree of *Capsicum annuum* cultivar 96P1938 which has an ornamental phenotype and produces fruit that is non-pungent.

FIG. 3 shows the pedigree that lead to non-pungent ornamental *Capsicum annuum* cultivar 96P610. As discussed in more detail herein, representative seed of 96P610 has been deposited with the ATCC. Plants grown from this seed produce *Capsicum annuum* plants that have a height that is less than or equal to 29.0 cm and fruit that is non-pungent. More specifically, the fruit produced by plants of *Capsicum annuum* plant 96P610 have a capsaicin level not greater than 500 Scoville Heat Units. Plants of 96P610 or parts from this plant, such as parts of these *Capsicum* annum plants, such as, but not limited to, seed, flowers, pollen, ovules, buds, shoots, cuttings, petals, leaves, stems, roots, tissues or combinations thereof, can be used in produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, 96P610 can be crossed, as either a male or female parent plant with a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. Methods for determining the levels of capsaicin in fruit, such as a pepper, are well known to those skilled in the art.

Plants that have a height equal to or less than about 29.0 cm and that have fruit having capsaicin levels not greater than about 500 Scoville Heat Units, that are produced by the above method and that are selected, are considered to be descendants of 96P610 (hereinafter referred to as "Descendant(s)"). Such Descendants can used to produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, a Descendant or a part from a Descendant, such as parts of these *Capsicum annuum* plants, such as, but not limited to, seed, flowers, pollen, ovules, buds, shoots, cuttings, petals, leaves, stems, roots, tissues or combinations thereof, can be crossed, as either a male or female parent plant with a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. Methods for determining the levels of capsaicin in fruit, such as a pepper, are well known to those skilled in the art. As those skilled in the art can appreciate, such breeding and selection methods described above can be repeated over and over to produce a variety of new *Capsicum annuum* plants having a height equal to or less than about 29.0 cm and that have fruit having capsaicin levels not greater than about 500 Scoville Heat Units.

Example 4

Pedigree for Non-Pungent Ornamental Pepper Cultivar 97P1938

Figure 4:
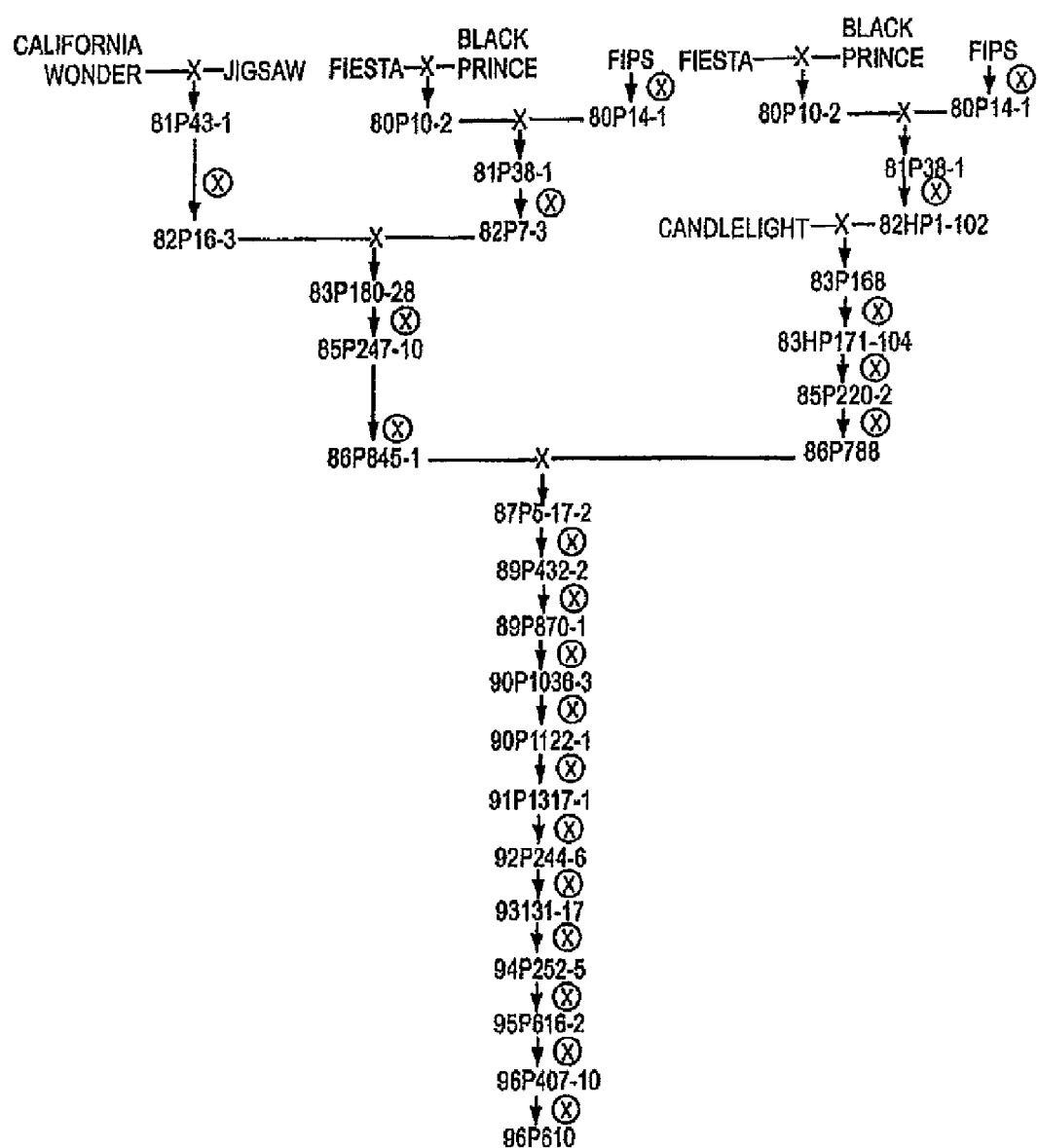
FIG. 4 shows the pedigree of *Capsicum annuum* cultivar 96P610 which has an ornamental phenotype and produces fruit that is non-pungent.

FIG. 4 shows the pedigree that lead to non-pungent ornamental *Capsicum annuum* cultivar 97P1938. As discussed in more detail herein, representative seed of 97P1938 has been deposited with the ATCC. Plants grown from this seed produce *Capsicum annuum* plants that have a height that is less than or equal to 29.0 cm and fruit that is non-pungent. More specifically, the fruit produced by plants of *Capsicum annuum* plant 97P1938 have a capsaicin level not greater than 500 Scoville Heat Units. Plants of 97P1938 or parts from this plant, such as parts of these *Capsicum* annum plants, such as, but not limited to, seed, flowers, pollen, ovules, buds, shoots, cuttings, petals, leaves, stems, roots, tissues or combinations thereof, can be used in produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, plants of 97P1938 can self-pollinated (also referred to as being "selfed" or "selfing") After said selfing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. Methods for determining the levels of capsaicin in fruit, such as a pepper, are well known to those skilled in the art.

Plants that have a height equal to or less than about 29.0 cm and that have fruit having capsaicin levels not greater than about 500 Scoville Heat Units, that are produced by the above method and that are selected, are considered to be descendants of 97P1938 (hereinafter referred to as "Descendant(s)"). Such Descendants can used to produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, a Descendant can self-pollinated. After said selfing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. Methods for determining the levels of capsaicin in fruit, such as a pepper, are well known to those skilled in the art. As those skilled in the art can appreciate, such breeding and selection methods described above can be repeated over and over to produce a variety of new *Capsicum annuum* plants having a height equal to or less than about 29.0 cm and that have fruit having capsaicin levels not greater than about 500 Scoville Heat Units.

Example 5

Pedigree for Non-Pungent Ornamental Pepper Cultivar 03P388-3

Figure 5:
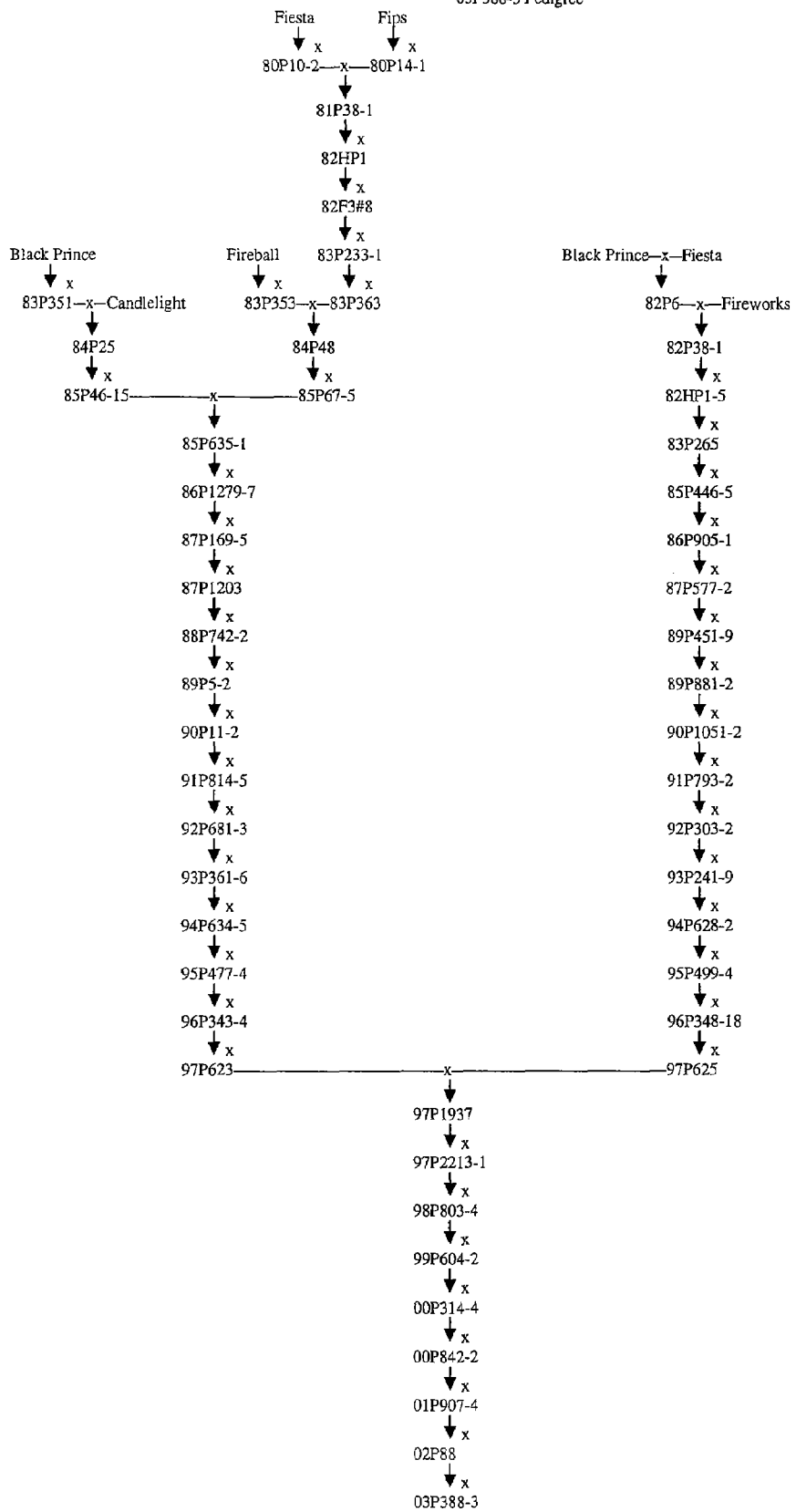
FIG. 5 shows the pedigree of *Capsicum annuum* cultivar 03P388-3 which has an ornamental phenotype and produces fruit that is non-pungent.

FIG. 5 shows the pedigree that lead to non-pungent ornamental *Capsicum annuum* cultivar 03P388-3. Plants of 03P388-3 have a height that is less than or equal to 29.0 cm and fruit that is non-pungent. More specifically, the fruit produced by plants of *Capsicum annuum* plant 03P388-3 have a capsaicin level not greater than 500 Scoville Heat Units. Plants of 03P388-3 or parts from this plant, such as parts of these *Capsicum annuum* plants, such as, but not limited to, seed, flowers, pollen, ovules, buds, shoots, cuttings, petals, leaves, stems, roots, tissues or combinations thereof, can be used in produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, 03P388-3 can be crossed, as either a male or female parent plant with a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. Methods for determining the levels of capsaicin in fruit, such as a pepper, are well known to those skilled in the art.

Plants that have a height equal to or less than about 29.0 cm and that have fruit having capsaicin levels not greater than about 500 Scoville Heat Units, that are produced by the above method and that are selected, are considered to be descendants of 03P388-3 (hereinafter referred to as "Descendant(s)"). Such Descendants can used to produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, a Descendant or a part from a Descendant, such as a part from a Descendant, such as parts of these *Capsicum annuum* plants, such as, but not limited to, seed, flowers, pollen, ovules, buds, shoots, cuttings, petals, leaves, stems, roots, tissues or combinations thereof, can be crossed, as either a male or female parent plant with a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected (hereinafter referred to as "Second Descendant(s)"). Methods for determining the levels of capsaicin in fruit, such as a pepper, are well known to those skilled in the art.

The Second Descendants selected above that have a height equal to or less than about 29.0 cm and that have fruit having capsaicin levels not greater than about 500 Scoville Heat Units can be used to produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/for backcrossing. For example, a Second Descendant or a part from a Second Descendant, such as parts of these *Capsicum annuum* plants, such as, but not limited to, seed, flowers, pollen, ovules, buds, shoots, cuttings, petals, leaves, stems, roots, tissues or combinations thereof, can be crossed, as either a male or female parent plant with a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. As those skilled in the art can appreciate, such breeding and selection methods described above can be repeated over and over to produce a variety of new *Capsicum annuum* plants having a height equal to or less than about 29.0 cm and that have fruit having capsaicin levels not greater than about 500 Scoville Heat Units.

Example 6

Pedigree for Non-Pungent Ornamental Pepper Cultivar 03P384-8

Figure 6:
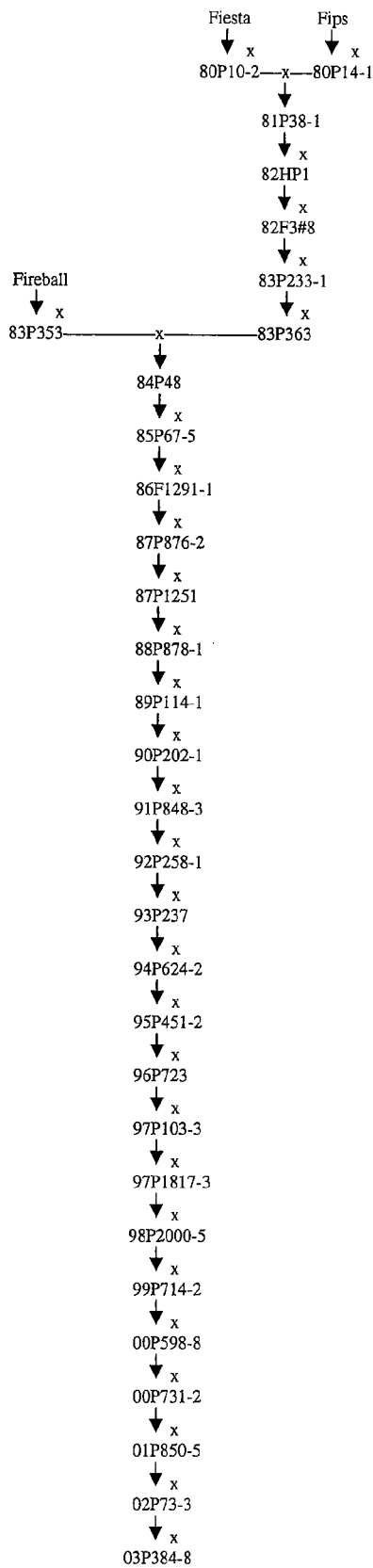
FIG. 6 shows the pedigree of *Capsicum annuum* cultivar 03P384-8 which has an ornamental phenotype and produces fruit that is non-pungent.

FIG. 6 shows the pedigree that lead to non-pungent ornamental *Capsicum annuum* cultivar 03P384-8. Plants of 03P384-8 have a height that is less than or equal to 29.0 cm and fruit that is non-pungent. More specifically, the fruit produced by plants of *Capsicum annuum* plant 03P384-8 have a capsaicin level not greater than 500 Scoville Heat Units. Plants of 03P384-8 or parts from this plant, such as parts of these *Capsicum annuum* plants, such as, but not limited to, seed, flowers, pollen, ovules, buds, shoots, cuttings, petals, leaves, stems, roots, tissues or combinations thereof, can be used in produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, pollen from 03P384-8 can be placed on the stigma of a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. Methods for determining the levels of capsaicin in fruit, such as a pepper, are well known to those skilled in the art.

Plants that have a height equal to or less than about 29.0 cm and that have fruit having capsaicin levels not greater than about 500 Scoville Heat Units, that are produced by the above method and that are selected, are considered to be descendants of 03P384-8 (hereinafter referred to as "Descendant(s)"). Such Descendants can used to produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, a Descendant or a part from a Descendant, such as parts of these *Capsicum annuum* plants, such as, but not limited to, seed, flowers, pollen, ovules, buds, shoots, cuttings, petals, leaves, stems, roots, tissues or combinations thereof, can be crossed, as either a male or female parent plant with a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected (hereinafter referred to as "Second Descendant(s)"). Methods for determining the levels of capsaicin in fruit, such as a pepper, are well known to those skilled in the art.

The Second Descendants selected above that have a height equal to or less than about 29.0 cm and that have fruit having capsaicin levels not greater than about 500 Scoville Heat Units can be used to produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, a cutting from a Second Descendant can be crossed, as either a male or female parent plant with a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. As those skilled in the art can appreciate, such breeding and selection methods described above can be repeated over and over to produce a variety of new *Capsicum annuum* plants having a height equal to or less than about 29.0 cm and that have fruit having capsaicin levels not greater than about 500 Scoville Heat Units.

Example 7

Evaluation of Capsaicin in Ornamental Pepper Cultivars

To evaluate the degree of pungency, capsaicin levels, as measured in Scoville Heat Units, were determined. For capsaicin analysis, fruit from ten pepper varieties were collected from greenhouse-grown material, and a commercial Sweet Green pepper was purchased locally. Plants were grown in a 1999 trial in Elburn, Ill. Included in the analysis were non-pungent ornamental peppers obtained from the plants described herein, specifically, 96P601, 96P610, 96P631 and 97P1938. Selection 96P611 is a parent of the hybrid pepper 97P1938. The varieties 'Red Missile', 'Masquerade' and 'Holiday Flame' were used as commercial ornamental pepper controls. Also evaluated was 'Triton', which is a non-pungent pepper marketed by Ball Horticultural Company, and A PI 'Sweet Orange' which was referred to in a publication as being a non-pungent ornamental pepper with "good ornamental characteristics" (See, Corley, W. L. and A. H. Dempsey, Ornamental Pepper Evaluation 1965-1971. University of Georgia College Agriculture Experiment Stations Research Report 136: 10 pp. (1972)).

For analysis, the pepper fruit were dried at 40° C. Three whole pepper fruits from three separate plants of each variety were ground into a fine powder and 200 mg was weighed and collected in a 5 ml tube. Two milliliters (mls) of methanol were added and mixed for 1 minute using a Prohomogenizer. The mixture was centrifuged and the supernatant passed through a 0.2 pm filter. Capsaicin levels were measured using HPLC. Samples of 50 µl were injected into a Supelcosil LC-18 25 cm×4.6 mm column and run at 1.5 ml/minute for 26 minutes using 60/40, methanol/water. Conditions and separation techniques followed the method of T. Cooper et al., *J. Agric. Food Chem.*, 39, 2253-2256 (1991). The results are shown below in Table 1.

TABLE 1

| Variety | Average Scoville Heat Units | Tukey Grouping ($\alpha = 0.05$) |
| --- | --- | --- |
| Sweet Green pepper | 96.8 | C |
| 'Red Missile' | 19708.3 | AB |
| 'Masquerade' | 36799.2 | A |
| 'Holiday Flame' | 34043.4 | A |
| 96P601 | 175.4 | C |
| 96P610 | 128.1 | C |
| 97P631 | 191.9 | C |
| 97P1938 | 121.9 | C |
| 96P611 | 137.9 | C |
| 'Triton' | 113.8 | C |
| 'Sweet Orange' | 5768.4 | B |

Analysis was completed using Tukey's Studentized Range Test and logarithmic transformed values of the original data. The analysis identified no significant difference between the Sweet Green pepper, 96P601, 96P610, 96P631, 97P1938, 96P611 or 'Triton'. The PI 'Sweet Orange' had a significantly higher capsaicin level than the ornamental peppers of the present invention, indicating that 'Sweet Orange' should not be classified as being non-pungent. The capsaicin levels of all non-pungent selections tested were significantly lower than the pungent ornamental controls 'Red Missile', 'Masquerade' and 'Holiday Flame'.

Example 8

Comparison of Ornamental Characteristics of Non-Pungent and Pungent Peppers

Six greenhouse plants of each cultivar listed in Table 2, below, were evaluated for fruit number, fruit weight, height, lateral branches, leaf length and leaf width. For fruit weight, five fruit from each of six plants were individually weighed and an average weight per plant was analyzed. For leaf length and leaf width, five mature basal leaves were measured and an average measurement per plant was analyzed. The three commercial pungent cultivars 'Red Missile', 'Holiday Flame' and 'Masquerade' were randomly selected. Plants were grown in a 1999 trial in Elburn, Ill. Means were compared using the Least Significant Different Test ($\alpha=0.05$). All non-pungent cultivars of the present invention possess ornamental characteristics that are statistically equivalent or superior to the commercial pungent ornamental peppers. In contrast, 'Triton' a non-pungent *Capsicum annuum* marketed by Ball Horticultural Company, does not possess the desirable phenotype of the commercial pungent ornamental *Capsicum annuum* plants. It has significantly less and larger fruit, it is significantly less branched, and has significantly longer and wider leaves than the commercial pungent ornamental *Capsicum annuum* plants. A PI 'Sweet Orange' was referred to in a publication as being a non-pungent ornamental *Capsicum*

*annuum* plant which had "good ornamental characteristics" (See, Corley, W. L. and A. H. Dempsey, Ornamental Pepper Evaluation 1965-1971. University of Georgia College of Agriculture Experiment Stations Research Report 136: 10 pp. (1972)). The ornamental characteristics of 'Sweet Orange' are statistically less desirable than commercial pungent ornamental *Capsicum annuum* plants for all characteristics evaluated.

gree breeding, recurrent selection or backcrossing, or genetic transformation or engineering, or breeding processes involving combinations of crossing, self-pollination and/or backcrossing. In particular, plants of *Capsicum annuum* 96P610 were crossed (96P610 was used as a male parent) with plants of *Capsicum annuum* cultivar 03P388-3 (which was used as a female parent). The resulting seeds produced from this cross were selected. The seeds were planted and grown into plants.

TABLE 2

| Variety | Fruit Number | 5% LSD LSD = 9.4 | Fruit Weight (g) | 5% LSD LSD = 1.5 | Plant Height (g) | 5% LSD LSD = 2.8 |
|---|---|---|---|---|---|---|
| 96P601 | 44.5 +/− 4.3 | b | 1.1 +/− 0.1 | a | 9.8 +/− 0.5 | a |
| 96P610 | 59.5 +/− 2.7 | cd | 0.8 +/− 0.1 | a | 8.9 +/− 0.9 | a |
| 96P631 | 83.2 +/− 15.1 | e | 0.9 +/− 0.1 | a | 19 +/− 1.3 | b |
| 97P1938 | 95.2 +/− 12.3 | ef | 1.1 +/− 0.1 | a | 26 +/− 2.8 | c |
| Red Missile | 51.7 +/− 4.9 | bc | 0.9 +/− 0.2 | a | 18.6 +/− 1.7 | b |
| Masquerade | 63.5 +/− 7.5 | d | 1.9 +/− 0.1 | a | 29.3 +/− 2.8 | d |
| Holiday Flame | 55.8 +/− 10.3 | cd | 1.8 +/− 0.3 | a | 18.7 +/− 2.7 | b |
| Triton | 7.8 +/− 1.5 | a | 14.1 +/− 2.5 | c | 18.5 +/− 2.2 | b |
| Sweet Orange | 10.5 +/− 5.7 | a | 10.6 +/− 3.0 | b | 35.5 +/− 4.6 | c |

| Variety | Lateral Branches | 5% LSD LSD = 1.2 | Leaf Length (cm) | 5% LSD LSD = 0.7 | Leaf Width (cm) | 5% LSD LSD = 0.4 |
|---|---|---|---|---|---|---|
| 96P601 | 7.7 +/− 0.5 | cd | 5.8 +/− 0.3 | a | 2.3 +/− 0.1 | a |
| 96P610 | 9.5 +/− 1.2 | e | 6.1 +/− 0.1 | a | 2.6 +/− 0.2 | a |
| 96P631 | 8.8 +/− 0.8 | de | 5.5 +/− 0.3 | a | 2.4 +/− 0.1 | a |
| 97P1938 | 11.8 +/− 1.2 | f | 7.0 +/− 0.4 | bc | 3.2 +/− 0.2 | b |
| Red Missile | 9.3 +/− 1.2 | e | 8.2 +/− 0.4 | d | 4.0 +/− 0.2 | c |
| Masquerade | 7.3 +/− 1.5 | c | 7.1 +/− 0.2 | bc | 3.3 +/− 0.1 | b |
| Holiday Flame | 7.3 +/− 1.0 | c | 7.6 +/− 0.6 | cd | 3.2 +/− 0.2 | b |
| Triton | 2.3 +/− 0.5 | a | 11.4 +/− 1.1 | e | 5.8 +/− 0.4 | e |
| Sweet Orange | 3.7 +/− 0.8 | b | 11.0 +/− 1.3 | e | 4.9 +/− 0.7 | d |

Example 9

Comparison of 'Sweet Pickle' and 96P611 Ornamental Characteristics

Figure 7:
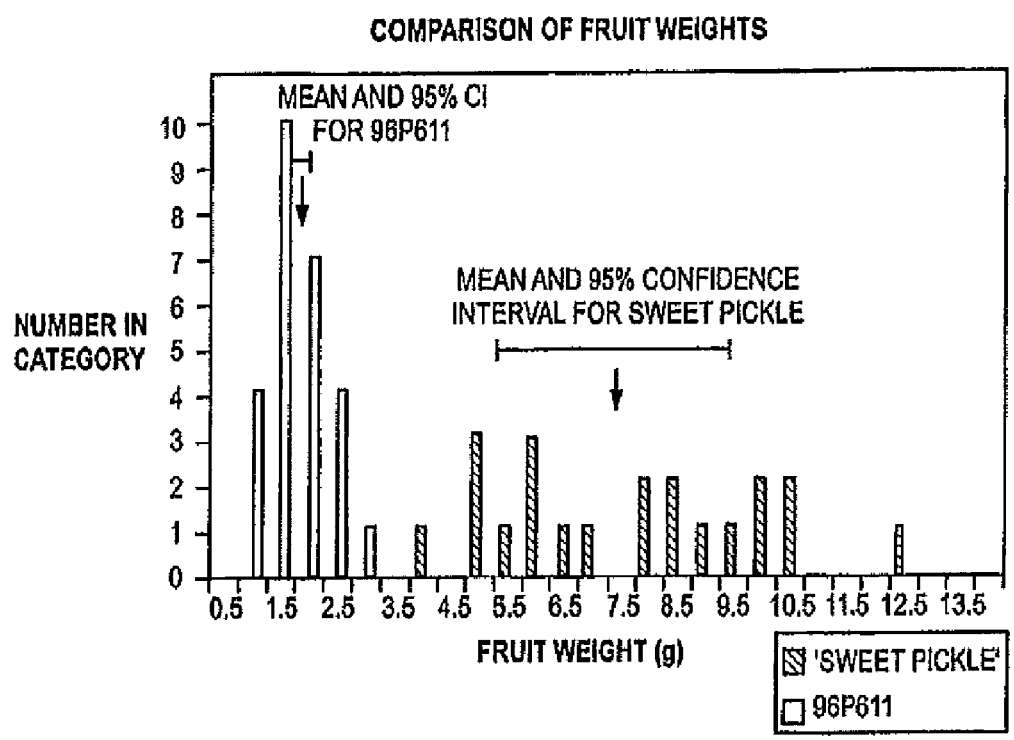
FIG. 7 shows a comparison of the fruit weights of 'Sweet Pickle' and cultivar 96P611 of the present invention.
Figure 8:
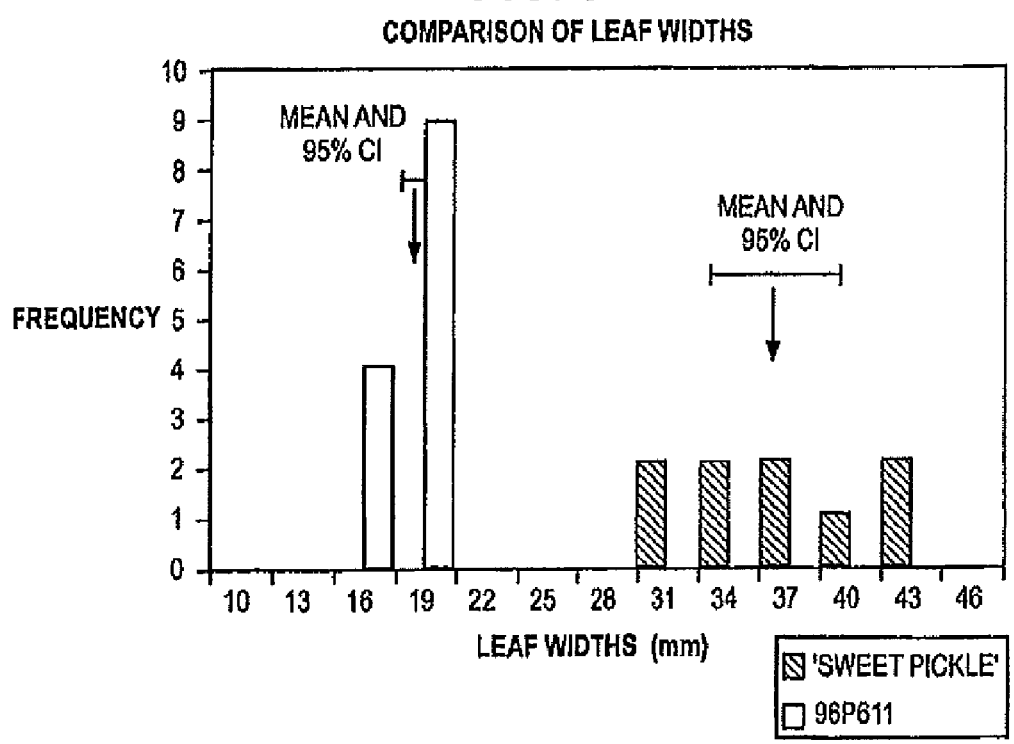
FIG. 8 shows a comparison of the leaf widths of 'Sweet Pickle' and cultivar 96P611 of the present invention.

The ornamental characteristics of 96P611, hybrid parent of 97P1938 of the present invention, were compared to 'Sweet Pickle' a non-pungent salad pepper marketed by Geo. W. Park Seed Co. Inc., 1 Parkton Avenue, Greenwood, S.C., 29647 using field grown plants from two replicated plots. Samples were evaluated for fruit weight, leaf width and leaf length. ANOVA results determined that differences between replicates were non-significant. Variation within samples from each variety was used to establish confidence intervals. As shown in FIGS. 7-9, cultivar 96P611 possesses the superior ornamental characteristics of smaller fruit weight and leave size when compared to 'Sweet Pickle'.

Example 10

Non-Pungent Ornamental Pepper Breeding

As discussed previously herein, all *Capsicum annuum* plants of the present invention, which have an ornamental phenotype and produce fruit that is non-pungent, maintain functional male and female sexual flower parts and can be used in breeding programs employing techniques that are well known to those skilled in the art, including, but not limited to, traditional plant breeding techniques, such as pedi- Then, *Capsicum annuum* plant 05P440 was selected. Plant 05P440 has ornamental characteristics, with non-pungent fruit (namely, the fruit have a capsaicin level of not greater than 500 Scoville Units), yellow immature fruit that turn red at maturity and a plant height of approximately 19 cm (from the soil line). The pedigree of female parent 03P388-3 is described in FIG. 5. In addition to being used in the above described cross, 03P388-3 is a parent of *Capsicum annuum* plant PA47 of the present invention. *Capsicum annuum* plant PA47 has an ornamental phenotype, namely, it has a height less than or equal to 29.0 cm (See Table 3 below). In addition, it has a mounded and spreading growth habit with purple conical fruit that mature to red.

TABLE 3

| Ornamental Traits | Measurement (cm) |
|---|---|
| Plant Height (from soil line) | 20.0 |
| Plant width | 66.7 |
| Leaf length (including petiole) | 6.8 |
| Leaf width | 2.0 |

The data in Table 3 were averaged from 10 plants grown in a summer field trial at Elburn, Ill. in 2005. In addition, approximately 20 grams of whole peppers from three plants of PA47 were sent to Silliker, Inc. for Scoville Heat Test analysis. Each sample was determined to have a capsaicin level of less than 1 Scoville Heat Unit.

The *Capsicum annuum* commercial hybrid 97P1938 of the present invention, which has an ornamental phenotype and produces fruit that is non-pungent, is the direct progenitor of several experimental lines currently being trialed for commercialization, including *Capsicum annuum* lines, 05P453, 05P454 and 05P605. These descendants of 97P1938 all have an ornamental phenotype and produce fruit that is non-pungent. These lines were developed from several years of selfing and selection from the original hybrid, 97P1938. These progeny are non-pungent, range from 19 to 34 cm in plant height and have long-conical to conical fruit that are yellow or purple in immature fruit color, maturing to red.

As shown in FIG. 4, the *Capsicum annuum* hybrid 97P1938 is the result of a cross between *Capsicum annuum* 96P623×*Capsicum annuum* 96P611. Parent line 96P611 continues to maintain functional male and female sexual flower parts and as exemplified herein, can be used to create not only the commercial hybrid 97P1938, but other new *Capsicum annuum* plants that have ornamental phenotypes and fruit that is non-pungent (namely, the fruit have a capsaicin level of not greater than 500 Scoville Units).

The *Capsicum annuum* hybrid PA47 of the present invention, which has an ornamental phenotype and has fruit that is non-pungent, is the result of a cross between *Capsicum annuum* plant 03P388-3, shown in FIG. 5, and *Capsicum annuum* plant 03P384-8, shown in FIG. 6. PA47 is deemed to be a commercial hybrid and is being used in a variety of breeding programs and is producing a number of descendants that exhibit an ornamental breeding phenotype and has fruit that is non-pungent. More specifically, PA47 has been self-pollinated. The seed resulting from this self-pollination have been collected. This seed was planted and a plant identified as 05P443 was selected. Line 05P443 is an experimental line that has an ornamental phenotype and produces brilliant purple fruit that are non-pungent (namely, the fruit have a capsaicin level of not greater than 500 Scoville Units). Characteristics of progeny from this pedigree are shown below in Table 4.

TABLE 4

| Selection | Plant width (cm) | Plant height (cm) | Leaf length (mm) | Leaf width (mm) | Fruit length (mm) | Fruit width (mm) |
|---|---|---|---|---|---|---|
| 453-3 | 48 | 34 | 43 | 18 | 50 | 7 |
| 454-2 | 41 | 28 | 49 | 19 | 36 | 10 |
| 605-1 | 36 | 19 | 39 | 18 | 35 | 8 |
| 440-1 | 25 | 19 | 50 | 18 | 48 | 11 |
| 443-3 | 61 | 28 | 32 | 14 | 38 | 9 |
| 443-9 | 33 | 15 | 41 | 18 | 38 | 13 |
| 368-1 | 46 | 20 | 25 | 12 | 18 | 6 |
| 418-5 | 23 | 15 | 36 | 17 | 52 | 7 |
| 427-5 | 36 | 17 | 28 | 11 | 16 | 8 |
| 428-1 | 43 | 18 | 27 | 10 | 14 | 10 |
| 514-1 | 71 | 28 | 39 | 20 | 22 | 12 |
| 520-1 | 30 | 15 | 35 | 18 | 27 | 8 |
| 520-2 | 46 | 18 | 32 | 13 | 30 | 5 |
| 523-3 | 28 | 17 | 45 | 16 | 42 | 6 |
| 524-3 | 30 | 24 | 41 | 18 | 38 | 5 |
| 544-1 | 41 | 11 | 22 | 9 | 16 | 8 |
| 553-4 | 41 | 15 | 32 | 11 | 40 | 8 |
| 558-4 | 56 | 24 | 28 | 12 | 19 | 8 |
| 574-5 | 71 | 33 | 33 | 14 | 28 | 8 |
| 590-6 | 30 | 18 | 28 | 12 | 28 | 7 |
| 590-7 | 33 | 15 | 32 | 14 | 40 | 7 |
| 610-10 | 33 | 18 | 40 | 15 | 25 | 8 |
| 616-1 | 33 | 18 | 44 | 16 | 38 | 5 |

Presently, there are 44 *Capsicum annuum* experimental lines that are descendents from other crosses involving the parent 03P384-8. Each of these experimental lines has an ornamental phenotype and produce fruit that are non-pungent (namely, the fruit have a capsaicin level of not more than 500 Scoville Units). There are also six (6) *Capsicum annuum* lines that are descendants of crosses involving the other parent, PA47. Each of these six *Capsicum annuum* lines have an ornamental phenotype and produce fruit that are non-pungent (namely, the fruit have a capsaicin level of not greater than 500 Scoville Units). These progeny range from 11 to 33 cm in plant height, have non-pungent fruit and exhibit extremely high fruitfulness as was characteristic of their parent (progeny range from having in excess of 95 to 600 fruit per plant).

From past and current breeding, it is abundantly clear that the *Capsicum annuum* plants of the present invention that have an ornamental phenotype and that produce fruit that is non-pungent are extremely useful in the breeding of subsequent lines (namely, descendants) of *Capsicum annuum* plants that have an ornamental phenotype and that produce fruit that is non-pungent. Using them as a source of plant breeding material in a plant breeding program for non-pungent ornamental peppers provides much more ornamental and promising progeny and a better breeding outcome than does the use of other non-pungent edible types as a donor of non-pungency. Hundreds of derivatives or descendants from these crosses have advanced through the breeding program and many persist today, on their way to being the subsequent generation of commercialized *Capsicum annuum* plants have an ornamental phenotype and fruit that is non-pungent.

Further Embodiments Of The Invention

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, which are inserted into the genome using transformation are referred to herein collectively as "transgenes". In some embodiments of the invention, a transgenic variant of 7925084 may contain at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Over the last fifteen to twenty years several methods for producing transgenic plants have been developed, and the present invention also relates to transgenic variants of the claimed ornamental non-pungent peppers.

One embodiment of the invention is a process for producing a non-pungent ornamental pepper plant comprising a desired trait, said process comprising transforming pepper hybrid PA47 with a transgene that confers a desired trait. Another embodiment is the product produced by this process. In one embodiment the desired trait may be one or more of herbicide resistance, insect resistance, disease resistance, or pest resistance. The specific gene may be any known in the art or listed herein, including; a polynucleotide conferring resistance to imidazolinone, sulfonylurea, glyphosate, glufosinate, triazine, benzonitrile, cyclohexanedione, phenoxy proprionic acid and L-phosphinothricin; a polynucleotide encoding a *Bacillus thuringiensis* polypeptide; or a polynucleotide conferring resistance to root-knot nematode, a fungus such as but not limited to *Phytophthora*, *Pythium*, *Rhizoctonia*, *Colletotrichum*, *Sclerotium*, or *Verticillium*; or a bacterium such as but not limited to *Erwinia* or *Xanthomonas*; or a virus such as but not limited to alfalfa mosaic virus (AMV), cucumber mosaic virus (CMV), potato virus X (PVX), potato virus Y (PVY), tobacco etch virus (TEV), and tobacco mosaic virus (TMV).

Numerous methods for plant transformation have been developed, including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88 and Armstrong, "The First Decade of Maize Transformation: A Review and Future Perspective" (*Maydica* 44:101-109, 1999). In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

A genetic trait which has been engineered into the genome of a particular *Capsicum annuum* plant may then be moved into the genome of another variety using traditional breeding techniques that are well known in the plant breeding arts. For example, a backcrossing approach is commonly used to move a transgene from a transformed *Capsicum annuum* variety into an already developed *Capsicum annuum* variety, and the resulting backcross conversion plant would then comprise the transgene(s).

Various genetic elements can be introduced into the plant genome using transformation. These elements include, but are not limited to genes, coding sequences, inducible, constitutive, and tissue specific promoters, enhancing sequences, and signal and targeting sequences. For example, see the traits, genes and transformation methods listed in U.S. Pat. No. 6,118,055.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed pepper plants using transformation methods as described below to incorporate transgenes into the genetic material of the pepper plant(s).

Expression Vectors for *Capsicum annuum* Transformation: Marker Genes

Expression vectors include at least one genetic marker operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley et al., *Proc. Natl. Acad. Sci. USA*, 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase and aminoglycoside-3′-adenyl transferase, the bleomycin resistance determinant (Hayford et al., *Plant Physiol.* 86:1216 (1988), Jones et al., *Mol. Gen. Genet.,* 210:86 (1987), Svab et al., *Plant Mol. Biol.* 14:197 (1990), Hille et al., *Plant Mol. Biol.* 7:171 (1986)). Other selectable marker genes confer resistance to herbicides such as glyphosate, glufosinate or bromoxynil (Comai et al., *Nature* 317:741-744 (1985), Gordon-Kamm et al., *Plant Cell* 2:603-618 (1990) and Stalker et al., *Science* 242:419-423 (1988)).

Selectable marker genes for plant transformation not of bacterial origin include, for example, mouse dihydrofolate reductase, plant 5-enolpyruvylshikimate-3-phosphate synthase and plant acetolactate synthase (Eichholtz et al., *Somatic Cell Mol. Genet.* 13:67 (1987), Shah et al., *Science* 233:478 (1986), Charest et al., *Plant Cell Rep.* 8:643 (1990)).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase (Jefferson, R. A., *Plant Mol. Biol. Rep.* 5:387 (1987), Teeri et al., *EMBO J.* 8:343 (1989), Koncz et al., *Proc. Natl. Acad. Sci. USA* 84:131 (1987), DeBlock et al., *EMBO J.* 3:1681 (1984)).

In vivo methods for visualizing GUS activity that do not require destruction of plant tissue are available (Molecular Probes publication 2908, IMAGENE GREEN, p. 1-4 (1993) and Naleway et al., *J. Cell Biol.* 115:151a (1991)). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells (Chalfie et al., *Science* 263: 802 (1994)). GFP and mutants of GFP may be used as screenable markers.

Expression Vectors for *Capsicum annuum* Transformation: Promoters

Genes included in expression vectors must be driven by a nucleotide sequence comprising a regulatory element, for example, a promoter. Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters that initiate transcription only in a certain tissue are referred to as "tissue-specific". A "cell-type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

A. Inducible Promoters—An inducible promoter is operably linked to a gene for expression in soybean. Optionally, the inducible promoter is operably linked to a nucleotide sequence encoding a signal sequence which is operably linked to a gene for expression in *Capsicum*. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Mett et al., *Proc. Natl. Acad. Sci. USA* 90:4567-4571 (1993)); In2 gene from maize which responds to benzenesulfonamide herbicide safeners (Hershey et al., *Mol. Gen. Genetics* 227:229-237 (1991) and Gatz et al., *Mol. Gen. Genetics* 243:32-38 (1994)) or Tet repressor from Tn10 (Gatz et al., *Mol. Gen. Genetics* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. USA* 88:0421 (1991)).

B. Constitutive Promoters—A constitutive promoter is operably linked to a gene for expression in *Capsicum* or the constitutive promoter is operably linked to a nucleotide sequence encoding a signal sequence which is operably linked to a gene for expression in *Capsicum*.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2: 163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)). The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO 96/30530.

C. Tissue-specific or Tissue-preferred Promoters—A tissue-specific promoter is operably linked to a gene for expression in *Capsicum*. Optionally, the tissue-specific promoter is operably linked to a nucleotide sequence encoding a signal sequence which is operably linked to a gene for expression in *Capsicum*. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter such as that from the phaseolin gene (Murai et al., *Science* 23:476-482 (1983) and Sengupta-Gopalan et al., *Proc. Natl. Acad. Sci. USA* 82:3320-3324 (1985)); a leaf-specific and light-induced promoter such as that from cab or rubisco (Simpson et al., *EMBO J.* 4(11): 2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of a protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., *Plant Mol. Biol.* 20:49 (1992); Knox, C., et al., *Plant Mol. Biol.* 9:3-17 (1987); Lerner et al., *Plant Physiol.* 91:124-129 (1989); Frontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., *Cell* 39:499-509 (1984); Steifel, et al., *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to an embodiment, the transgenic plant provided for commercial production of foreign protein is a *Capsicum annuum* plant. In another embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology*, CRC Press, Boca Raton 269:284 (1993). Map information concerning chromosomal location is useful for proprietary protection of a subject transgenic plant.

Wang et al. discuss "Large Scale Identification, Mapping and Genotyping of Single-Nucleotide Polymorphisms in the Human Genome", *Science*, 280:1077-1082, 1998, and similar capabilities are becoming increasingly available for the soybean genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons would involve hybridizations, RFLP, PCR, SSR and sequencing, all of which are conventional techniques. SNPs may also be used alone or in combination with other techniques.

Likewise, by means of the present invention, plants can be genetically engineered to express various phenotypes of agronomic interest. Through the transformation of *Capsicum annuum* the expression of genes can be altered to enhance disease resistance, insect resistance, herbicide resistance, pest resistance and other traits. Transformation can also be used to insert DNA sequences which control or help control male-sterility. DNA sequences native to *Capsicum annuum* as well as non-native DNA sequences can be transformed into *Capsicum annuum* and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including but not limited to knock-outs (such as by insertion of a transposable element such as mu (Vicki Chandler, The Maize Handbook ch. 118 (Springer-Verlag 1994) or other genetic elements such as a FRT, Lox or other site specific integration site, antisense technology (see, e.g., Sheehy et al. (1988) *PNAS USA* 85:8805-8809; and U.S. Pat. Nos. 5,107,065; 5,453,566; and 5,759,829); co-suppression (e.g., Taylor (1997) *Plant Cell* 9:1245; Jorgensen (1990) *Trends Biotech.* 8(12):340-344; Flavell (1994) *PNAS USA* 91:3490-3496; Finnegan et al. (1994) *Bio/Technology* 12: 883-888; and Neuhuber et al. (1994) *Mol. Gen. Genet.* 244: 230-241); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *PNAS USA* 95:15502-15507), virus-induced gene silencing (Burton, et al. (2000) *Plant Cell* 12:691-705; and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; and WO 98/53083); MicroRNA (Aukerman & Sakai (2003) *Plant Cell* 15:2730-2741); ribozymes (Steinecke et al. (1992) *EMBO J.* 11:1525; and Perriman et al. (1993) *Antisense Res. Dev.* 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

By means of the present invention, various genes of interest can be expressed in transformed plants. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with one or more cloned resistance genes to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. *tomato* encodes a protein kinase); Mindrinos et al. *Cell* 78:1089 (1994) (*Arabidopsis* RSP2 gene for resistance to *Pseudomonas syringae*), McDowell & Woffenden, (2003) *Trends Biotechnol.* 21(4): 178-83 and Toyoda et al., (2002) *Transgenic Res.* 11 (6):567-82.

B. A gene conferring resistance to a pest, such as root-knot nematode. See e.g., PCT Application WO 96/30517; PCT Application WO 93/19181.

C. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, Van Damme et al., *Plant Molec. Biol.* 24:25 (1994), who disclose the nucleotide sequences of several *Clivia miniata* mannose-binding lectin genes.

E. A vitamin-binding protein such as avidin. See PCT application US 93/06487 which teaches the use of avidin and avidin homologues as larvicides against insect pests.

F. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G. An insect-specific hormone or pheromone such as an ecdysteroid or juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*); Chattopadhyay et al. (2004) *Critical Reviews in Microbiology* 30 (1): 33-54 2004; Zjawiony (2004) *J Nat Prod* 67 (2): 300-310; Carlini & Grossi-de-Sa (2002) *Toxicon*, 40 (11): 1515-1539; Ussuf et al. (2001) *Curr Sci.* 80 (7): 847-853; and Vasconcelos & Oliveira (2004) *Toxicon* 44 (4): 385-403. See also U.S. Pat. No. 5,266,317 to Tomalski et al., which discloses genes encoding insect-specific, paralytic neurotoxins.

I. An insect-specific venom produced in nature by a snake, a wasp, etc. For example, see Pang et al., *Gene* 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 (Scott et al.), which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene, U.S. Pat. Nos. 7,145,060, 7,087,810 and 6,563,020.

L. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

M. A hydrophobic moment peptide. See PCT application WO 95/16776 and U.S. Pat. No. 5,580,852, which disclose peptide derivatives of tachyplesin which inhibit fungal plant pathogens, and PCT application WO 95/18855 and U.S. Pat. No. 5,607,914 which teaches synthetic antimicrobial peptides that confer disease resistance.

N. A membrane permease, a channel former or a channel blocker. For example, see the disclosure of Jaynes et al., *Plant Sci* 89:43 (1993), of heterologous expression of a cecropin-β lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus and tobacco mosaic virus.

P. An insect-specific antibody or an immunotoxin derived therefrom. Thus, an antibody targeted to a critical metabolic function in the insect gut would inactivate an affected enzyme, killing the insect. See Taylor et al., Abstract #497, *Seventh Int'l Symposium on Molecular Plant-Microbe Interactions* (Edinburgh, Scotland) (1994) (enzymatic inactivation in transgenic tobacco via production of single-chain antibody fragments).

Q. A virus-specific antibody. See, for example, Tavladoraki et al., *Nature* 366:469 (1993), who show that transgenic plants expressing recombinant antibody genes are protected from virus attack.

R. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

S. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

T. Genes involved in the Systemic Acquired Resistance (SAR) Response and/or the pathogenesis-related genes. Briggs, S., *Current Biology,* 5(2) (1995); Pieterse & Van Loon (2004) *Curr. Opin. Plant Bio.* 7(4):456-64 and Somssich (2003) *Cell* 113(7):815-6.

U. Antifungal genes. See Cornelissen and Melchers, *Plant Physiol.,* 101:709-712 (1993); Parijs et al., *Planta* 183:258-264 (1991) and Bushnell et al., *Can. J. of Plant Path.* 20(2): 137-149 (1998). Also see U.S. Pat. No. 6,875,907.

V. Detoxification genes, such as for fumonisin, beauvericin, moniliformin and zearalenone and their structurally related derivatives. For example, see U.S. Pat. No. 5,792,931.

W. Cystatin and cysteine proteinase inhibitors. See U.S. Pat. No. 7,205,453.

X. Defensin genes. See WO 03/000863 and U.S. Pat. No. 6,911,577.

Y. Genes conferring resistance to nematodes, and in particular root-knot nematodes. See e.g. PCT Application WO 96/30517; PCT Application WO 93/19181, WO 03/033651 and Urwin et al., *Planta* 204:472-479 (1998), Williamson (1999) *Curr Opin Plant Bio.* 2(4):327-31.

Z. Genes that confer resistance to *Phytophthora* root rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al., *Phytophthora* Root Rot Resistance Gene Mapping in Soybean, Plant Genome IV Conference, San Diego, Calif. (1995).

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance conferred by mutant 5-enolpyruvlshikimate-3-phosphate synthase (EPSPS) and aroA genes, respectively) and other phosphono compounds such as glufosinate (phosphinothricin acetyl transferase (PAT) and *Streptomyces hygroscopicus* PAT bar genes), and pyridinoxy or phenoxy proprionic acids and cyclohexanediones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,566,587; 6,338,961; 6,248,876 B1; 6,040,497; 5,804, 425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications EP1173580; WO 01/66704; EP1173581 and EP1173582, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463, 175, which are incorporated herein by reference for this purpose. In addition glyphosate resistance can be imparted to plants by the over expression of genes encoding glyphosate N-acetyltransferase. See, for example, U.S. application Ser. No. 10/427,692. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No.

4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., *Bio/Technology* 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2, and Acc2-S3 genes described by Marshall et al., *Theor. Appl. Genet.* 83:435 (1992).

C. An herbicide that inhibits photosynthesis, such as a triazine (psbA and gs+ genes) and a benzonitrile (nitrilase gene). Przibila et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441 and 67442. Cloning and expression of DNA coding for a glutathione S-transferase is described by Hayes et al., *Biochem. J.* 285:173 (1992).

D. Acetohydroxy acid synthase, which has been found to make plants that express this enzyme resistant to multiple types of herbicides, has been introduced into a variety of plants. See Hattori et al., *Mol. Gen. Genet.* 246:419, 1995. Other genes that confer tolerance to herbicides include a gene encoding a chimeric protein of rat cytochrome P4507A1 and yeast NADPH-cytochrome P450 oxidoreductase (Shiota et al., *Plant Physiol.,* 106:17, 1994), genes for glutathione reductase and superoxide dismutase (Aono et al., *Plant Cell Physiol.* 36:1687, 1995), and genes for various phosphotransferases (Datta et al., *Plant Mol. Biol.* 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

3. Genes that Control Male Sterility

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

A. Introduction of a deacetylase gene under the control of a tapetum-specific promoter and with the application of the chemical N—Ac—PPT. See international publication WO 01/29237.

B. Introduction of various stamen-specific promoters. See international publications WO 92/13956 and WO 92/13957.

C. Introduction of the barnase and the barstar genes. See Paul et al., *Plant Mol. Biol.* 19:611-622, 1992).

For additional examples of nuclear male and female sterility systems and genes, see also, U.S. Pat. No. 5,859,341; U.S. Pat. No. 6,297,426; U.S. Pat. No. 5,478,369; U.S. Pat. No. 5,824,524; U.S. Pat. No. 5,850,014; and U.S. Pat. No. 6,265,640; all of which are hereby incorporated by reference.

5. Genes that Create a Site for Site-Specific DNA Integration.

This includes the introduction of FRT sites that may be used in the FLP/FRT system and/or Lox sites that may be used in the Cre/Loxp system. For example, see Lyznik, et al., Site-Specific Recombination for Genetic Engineering in Plants, *Plant Cell Rep* (2003) 21:925-932 and WO 99/25821, which are hereby incorporated by reference. Other systems that may be used include the Gin recombinase of phage Mu (Maeser et al., 1991; Vicki Chandler, The Maize Handbook ch. 118 (Springer-Verlag 1994), the Pin recombinase of *E. coli* (Enomoto et al., 1983), and the R/RS system of the pSR1 plasmid (Araki et al., 1992).

6. Genes that Affect Abiotic Stress Resistance.

Genes that affect abiotic stress resistance (including but not limited to flowering and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. No. 5,892,009, U.S. Pat. No. 5,965,705, U.S. Pat. No. 5,929,305, U.S. Pat. No. 5,891,859, U.S. Pat. No. 6,417,428, U.S. Pat. No. 6,664,446, U.S. Pat. No. 6,706,866, U.S. Pat. No. 6,717,034, U.S. Pat. No. 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; US 2004/0148654 and WO 01/36596 where abscisic acid is altered in plants resulting in improved plant phenotype such as increased yield and/or increased tolerance to abiotic stress; WO 2000/006341, WO 04/090143, U.S. application Ser. No. 10/817,483 and U.S. Pat. No. 6,992,237 where cytokinin expression is modified resulting in plants with increased stress tolerance, such as drought tolerance, and/or increased yield. Also see WO 02/02776, WO 2003/052063, JP2002281975, U.S. Pat. No. 6,084,153, WO 01/64898, U.S. Pat. Nos. 6,177,275 and 6,107,547 (enhancement of nitrogen utilization and altered nitrogen responsiveness). For ethylene alteration, see US 20040128719, US 20030166197 and WO 2000/32761. For plant transcription factors or transcriptional regulators of abiotic stress, see e.g. US 20040098764 or US 20040078852.

Other genes and transcription factors that affect plant growth and agronomic traits such as yield, flowering, plant growth and/or plant structure, can be introduced or introgressed into plants, see e.g. WO 97/49811 (LHY), WO 98/56918 (ESD4), WO 97/10339 and U.S. Pat. No. 6,573,430 (TFL), U.S. Pat. No. 6,713,663 (FT), WO 96/14414 (CON), WO 96/38560, WO 01/21822 (VRN1), WO 00/44918 (VRN2), WO 99/49064 (GI), WO 00/46358 (FRI), WO 97/29123, U.S. Pat. No. 6,794,560, U.S. Pat. No. 6,307,126

(GAI), WO 99/09174 (D8 and Rht), and WO 2004/076638 and WO 2004/031349 (transcription factors).

Methods for *Capsicum annuum* Transformation

Numerous methods for plant transformation have been developed including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc. Boca Raton, 1993) pages 67-88. In addition, expression vectors and in-vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra and Moloney et al., *Plant Cell Reports* 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation where DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987); Sanford, J. C., *Trends Biotech.* 6:299 (1988); Klein et al., *Bio/Tech.* 6:559-563 (1988); Sanford, J. C. *Physiol Plant* 7:206 (1990); Klein et al., *Biotechnology* 10:268 (1992). See also U.S. Pat. No. 5,015,580 (Christou, et al.), issued May 14, 1991 and U.S. Pat. No. 5,322,783 (Tomes, et al.), issued Jun. 21, 1994.

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.*, 4:2731 (1985); Christou et al., *Proc Natl. Acad. Sci. USA* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues have also been described (Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994)).

Following transformation of *Capsicum annuum* target tissues, expression of the above-described selectable marker genes allows for preferential selection of transformed cells, tissues and/or plants, using regeneration and selection methods well known in the art.

The foregoing methods for transformation would typically be used for producing a transgenic variety. The transgenic variety could then be crossed with another (non-transformed or transformed) variety in order to produce a new transgenic variety. Alternatively, a genetic trait that has been engineered into a particular *Capsicum annuum* line using the foregoing transformation techniques could be moved into another line using traditional backcrossing techniques that are well known in the plant breeding arts. For example, a backcrossing approach could be used to move an engineered trait from a public variety into a proprietary variety, or from a variety containing a foreign gene in its genome into a variety or varieties that do not contain that gene. As used herein, "crossing" can refer to a simple X by Y cross or the process of backcrossing depending on the context.

Genetic Marker Profile Through SSR and First Generation Progeny

In addition to phenotypic observations, a plant can also be identified by its genotype. The genotype of a plant can be characterized through a genetic marker profile which can identify plants of the same variety or a related variety or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Paran, I., et al. 1998. *Euphytica*. 99:167-173 and Kumar, L. D. et al. 2001. *Forensic Sci. Int.* 116:63-68, each of which are incorporated by reference herein in their entirety.

Particular markers used for these purposes are not limited to any particular set of markers, but are envisioned to include any type of marker and marker profile which provides a means of distinguishing varieties. The genetic marker profile is also useful in breeding and developing backcross conversions.

The present invention comprises one or more *Capsicum annuum* plants characterized by molecular and physiological data obtained from the representative sample of said varieties (96P610, 97P1938, 96P611 and PA47) deposited with the American Type Culture Collection (ATCC).

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties it is preferable if all SSR profiles are performed in the same lab.

Primers used are publicly available and may be found in Paran, I., et al. 1998. *Euphytica.* 99:167-173 and Kumar, L. D. et al. 2001. *Forensic Sci. Int.* 116:63-68, the disclosures of which are incorporated herein by reference.

The SSR profiles of *Capsicum annuum* plants 96P610, 97P1938, 96P611 and PA47 can be used to identify plants comprising any of 96P610, 97P1938, 96P611 or PA47 as a parent, since such plants will comprise the same homozygous alleles as 96P610, 97P1938, 96P611 or PA474. Because each individual *Capsicum annuum* variety is essentially homozygous at all relevant loci, most loci should have only one type of allele present. In contrast, a genetic marker profile of an $F_1$ progeny should be the sum of those parents, e.g., if one parent was homozygous for allele x at a particular locus, and the other parent homozygous for allele y at that locus, then the $F_1$ progeny will be xy (heterozygous) at that locus. Subsequent generations of progeny produced by selection and breeding are expected to be of genotype x (homozygous), y (homozygous), or xy (heterozygous) for that locus position. When the $F_1$ plant is selfed or sibbed for successive filial generations, the locus should be either x or y for that position.

In addition, plants and plant parts substantially benefiting from the use of any of *Capsicum annuum* varieties 96P610, 97P1938, 96P611 or PA47 in their development comprising a backcross conversion, transgene, or genetic sterility factor, may be identified by having a molecular marker profile with a high percent identity to any of 96P610, 97P1938, 96P611 or PA47 depending on which was used as a parent. Such a percent identity might be 95%, 96%, 97%, 98%, 99%, 99.5% or 99.9% identical to 96P610, 97P1938, 96P611 or PA47.

The SSR profiles of *Capsicum annuum* varieties 96P610, 97P1938, 96P611 and PA47 also can be used to identify essentially derived varieties and other progeny varieties developed from the use of 96P610, 97P1938, 96P611 or PA47 as a parent, as well as cells and other plant parts thereof. Progeny plants and plant parts produced using any of 96P610, 97P1938, 96P611 or PA47 as a parent may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from *Capsicum annuum* variety 96P610, 97P1938, 96P611 or PA47, as measured by either percent identity or percent similarity. Such progeny may be further characterized as being within a pedigree distance of 96P610, 97P1938, 96P611 or PA47, such as within 1, 2, 3, 4 or 5 or less cross-pollinations to a *Capsicum annuum* plant other than 96P610, 97P1938, 96P611 or PA47 or a plant that has 96P610, 97P1938, 96P611 or PA47 as a progenitor. Unique molecular profiles may be identified with other molecular tools such as SNPs and RFLPs.

While determining the SSR genetic marker profile of the plants described supra, several unique SSR profiles may also be identified which did not appear in either parent of such plant. Such unique SSR profiles may arise during the breeding process from recombination or mutation. A combination of several unique alleles provides a means of identifying a plant variety, an $F_1$ progeny produced from such variety, and progeny produced from such variety.

Introduction of a New Trait or Locus

*Capsicum annuum* varieties 96P610, 97P1938, 96P611 and PA47 represent new base genetic varieties into which a new locus or trait may be introgressed. Direct transformation and backcrossing represent two important methods that can be used to accomplish such an introgression. The term backcross conversion and single locus conversion are used interchangeably to designate the product of a backcrossing program.

Tissue Culture

Further reproduction of *Capsicum annuum* varieties 96P610, 97P1938, 96P611 and PA47 can occur by tissue culture and regeneration. Tissue culture of various tissues of *Capsicum annuum* and regeneration of plants therefrom is well known and widely published. For example, reference may be had to Agrawal, S. et al. 1989. *Plant Cell, Tissue and Organ Culture.* 16:47-55; Badhipadma, K. et al. 2003. *In Vitro Cell Dev. Bio Plant.* 39:536-539; Sanatombi, K. et al. 2007. *Scientia Hort.* 113:96-99 and U.S. Pat. No. 5,008,200 issued Apr. 16, 1991 to Ranch et al. Thus, another aspect of this invention is to provide cells which upon growth and differentiation produce *Capsicum annuum* plants having the physiological and morphological characteristics of *Capsicum annuum* hybrid PA47.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, petioles, leaves, stems, roots, root tips, anthers, pistils and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

Deposit Information

Two thousand five hundred (2500) seeds of *Capsicum annuum* plant 96P610 which exhibits an ornamental phenotype and produces fruit that is non-pungent have been placed on deposit with the American Type Culture Collection (ATCC), 10801 University Blvd., Manassas, Va., 20110-2209 under Deposit Accession Number 203779 on Feb. 17, 1999. This deposit was made in compliance with the Budapest Treaty requirements that the duration of the deposit should be for thirty (30) years from the date of deposit or for five (5) years after the last request for the deposit at the depository or for the enforceable life of a U.S. patent that matures from this application, whichever is longer. The deposit of these *Capsicum annuum* seeds will be replenished should it become non-viable at the depository.

Two thousand five hundred (2500) seeds of *Capsicum annuum* plant 97P1938 which exhibits an ornamental phenotype and produces fruit that is non-pungent have been placed on deposit with the American Type Culture Collection (ATCC), 10801 University Blvd., Manassas, Va., 20110-2209 under Deposit Accession Number PTA-5749 on Jan. 7, 2004. This deposit was made in compliance with the Budapest Treaty requirements that the duration of the deposit should be for thirty (30) years from the date of deposit or for five (5) years after the last request for the deposit at the depository or for the enforceable life of a U.S. patent that matures from this application, whichever is longer. The deposit of these *Capsicum annuum* seeds will be replenished should it become non-viable at the depository.

Two thousand five hundred (2500) seeds of *Capsicum annuum* plant 96P611 which exhibits an ornamental phenotype and produces fruit that is non-pungent have been placed on deposit with the American Type Culture Collection (ATCC), 10801 University Blvd., Manassas, Va., 20110-2209 under Deposit Accession Number PTA-5689 on Dec. 8, 2003. This deposit was made in compliance with the Budapest Treaty requirements that the duration of the deposit should be for thirty (30) years from the date of deposit or for five (5) years after the last request for the deposit at the depository or for the enforceable life of a U.S. patent that matures from this application, whichever is longer. The deposit of these *Capsicum annuum* seeds will be replenished should it become non-viable at the depository.

Two thousand five hundred (2500) seeds of *Capsicum annuum* plant PA47 which exhibits an ornamental phenotype and produces fruit that is non-pungent have been placed on deposit with the American Type Culture Collection (ATCC), 10801 University Blvd., Manassas, Va., 20110-2209 under Deposit Accession Number PTA-8808 on Dec. 5, 2007. This deposit was made in compliance with the Budapest Treaty requirements that the duration of the deposit should be for thirty (30) years from the date of deposit or for five (5) years after the last request for the deposit at the depository or for the enforceable life of a U.S. patent that matures from this application, whichever is longer. The deposit of these *Capsicum annuum* seeds will be replenished should it become non-viable at the depository.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

What is claimed is:

1. A seed of *Capsicum annuum* hybrid designated PA47, wherein a representative sample of seed of said hybrid was deposited under ATCC Accession No. PTA-8808.

2. A *Capsicum annuum* plant, or a part thereof, produced by growing the seed of claim 1.

3. A tissue culture produced from protoplasts or cells from the plant of claim 2, wherein said cells or protoplasts of the tissue culture are produced from a plant part selected from the group consisting of leaf, pollen, embryo, cotyledon, hypocotyl, meristematic cell, root, root tip, pistil, anther, flower, shoot, stem, fruit and petiole.

4. A *Capsicum annuum* plant regenerated from the tissue culture of claim 3, wherein the plant has all of the morphological and physiological characteristics of PA47.

5. A method for producing a *Capsicum annuum* seed comprising crossing two *Capsicum annuum* plants and harvesting the resultant *Capsicum annuum* seed, wherein at least one *Capsicum annuum* plant is the *Capsicum annuum* plant of claim 2.

6. A *Capsicum annuum* seed produced by the method of claim 5.

7. A method for producing a *Capsicum annuum* plant that contains in its genetic material one or more transgenes, wherein the method comprises crossing the *Capsicum annuum* plant of claim 2 with either a second *Capsicum annuum* plant which contains a transgene or a transformed *Capsicum annuum* plant of the hybrid PA47, so that the genetic material of the progeny that results from the cross contains the transgene(s) operably linked to a regulatory element and wherein the transgene confers a trait selected from the group consisting of male sterility, male fertility, herbicide resistance, insect resistance, disease resistance, pest resistance, and ornamental phenotype.

8. A method of producing an inbred pepper plant derived from the hybrid pepper variety PA47, the method comprising the steps of:
   a. preparing a progeny plant derived from hybrid pepper variety PA47 by crossing the plant of claim 2 with a second pepper plant;
   b. crossing the progeny plant with itself or a second pepper plant to produce a seed of a progeny plant of a subsequent generation;
   c. growing a progeny plant of a subsequent generation from said seed and crossing the progeny plant of a subsequent generation with itself or a second pepper plant; and
   d. repeating step b) or c) for at least 1 more generation to produce an inbred pepper plant derived from the hybrid pepper variety PA47.

* * * * *